US012733980B2

(12) United States Patent
Borsic

(10) Patent No.: US 12,733,980 B2
(45) Date of Patent: Sep. 15, 2026

(54) SYSTEM AND METHOD FOR ABLATION TREATMENT OF TISSUE WITH INTERACTIVE GUIDANCE

(71) Applicant: NE Scientific, Inc., Andover, MA (US)

(72) Inventor: Andrea Borsic, Turin (IT)

(73) Assignee: NE Scientific, Inc., Andover, MA (US)

( * ) Notice: Subject to any disclaimer, the term of this patent is extended or adjusted under 35 U.S.C. 154(b) by 256 days.

(21) Appl. No.: 18/267,169

(22) PCT Filed: Dec. 14, 2021

(86) PCT No.: PCT/US2021/063257
§ 371 (c)(1),
(2) Date: Jun. 14, 2023

(87) PCT Pub. No.: WO2022/132730
PCT Pub. Date: Jun. 23, 2022

(65) Prior Publication Data

US 2024/0058062 A1 Feb. 22, 2024

Related U.S. Application Data

(60) Provisional application No. 63/136,808, filed on Jan. 13, 2021, provisional application No. 63/125,472, (Continued)

(51) Int. Cl.

| | |
|---|---|
| ***A61B 34/10*** | (2016.01) |
| ***A61B 18/14*** | (2006.01) |
| ***A61B 90/00*** | (2016.01) |
| ***G06T 7/00*** | (2017.01) |
| ***G06T 7/62*** | (2017.01) |
| ***G06T 19/00*** | (2011.01) |
| ***G06T 19/20*** | (2011.01) |

(Continued)

(52) U.S. Cl.
CPC ............. *A61B 34/10* (2016.02); *A61B 18/14* (2013.01); *A61B 90/37* (2016.02); *G06T 7/0012* (2013.01); *G06T 7/62* (2017.01); *G06T 19/003* (2013.01); *G06T 19/20* (2013.01); *G16H 50/50* (2018.01); *A61B 2018/00577* (2013.01); *A61B 2034/104* (2016.02); *A61B 2034/105* (2016.02); *A61B 2034/107* (2016.02); *G06T 2207/30096* (2013.01); *G06T 2219/2004* (2013.01)

(58) Field of Classification Search
CPC ......... A61B 34/10; A61B 90/37; G16H 50/50
See application file for complete search history.

(56) References Cited

U.S. PATENT DOCUMENTS

| | | | |
|---|---|---|---|
| 2014/0081114 | A1 | 3/2014 | Shachar et al. |
| 2016/0022369 | A1 | 1/2016 | Audigier et al. |

(Continued)

*Primary Examiner* — Rochelle D Turchen
(74) *Attorney, Agent, or Firm* — Pandiscio & Pandiscio

(57) ABSTRACT

A system and method of modeling a necrotized tissue in an ablation procedure, the method comprising providing, at a computational component, a computer model of a volume of human tissue, simulating, by the computational component, an ablation site in the computer model, determining, by the computational component, a deposited power density relating to at least an ablation parameter using at least an ablation mode, determining, by the computational component, a heat distribution at the ablation site as a function of the deposited power density, and identifying, by the computational component, a volume of tissue necrotized during an ablation procedure performed at the ablation site.

9 Claims, 10 Drawing Sheets

Related U.S. Application Data filed on Dec. 15, 2020, provisional application No. 63/125,498, filed on Dec. 15, 2020.

(51) Int. Cl.

| | |
|---|---|
| ***G16H 50/50*** | (2018.01) |
| *A61B 18/00* | (2006.01) |

(56) References Cited

U.S. PATENT DOCUMENTS

| | | | |
|---|---|---|---|
| 2017/0049508 | A1 | 2/2017 | Long et al. |
| 2019/0371474 | A1 | 12/2019 | Borsic |
| 2020/0237421 | A1 | 7/2020 | Ataman et al. |

SYSTEM AND METHOD FOR ABLATION TREATMENT OF TISSUE WITH INTERACTIVE GUIDANCE

CROSS-REFERENCE TO RELATED APPLICATIONS

This application is a 371 national stage entry of pending prior International (PCT) Patent Application No. PCT/US2021/063257, filed Dec. 14, 2021 by NE Scientific, LLC for SYSTEM AND METHOD FOR ABLATION TREATMENT OF TISSUE WITH INTERACTIVE GUIDANCE, which patent application, in turn claims the benefit of (i) U.S. Provisional Patent Application Ser. No. 63/136,808, filed on Jan. 13, 2021, titled "SYSTEM AND METHOD FOR ABLATION TREATMENT OF TISSUE WITH INTERACTIVE GUIDANCE,"; (ii) U.S. Provisional Patent Application Ser. No. 63/125,472, filed on Dec. 15, 2020, titled "SYSTEMS AND METHODS FOR SIMULATION AN ABLATION VOLUME,"; and (iii) U.S. Provisional Patent Application Ser. No. 63/125,498, filed on Dec. 15, 2020, titled "SYSTEMS AND METHODS FOR DETERMINING AN ABLATION FOOTPRINT,". The four (4) above-identified patent applications are hereby incorporated herein by reference.

STATEMENT REGARDING FEDERALLY SPONSORED RESEARCH OR DEVELOPMENT

This invention was made with government support under R44 CA189515 awarded by the National Institutes of Health. The government has certain rights in the invention.

FIELD OF THE INVENTION

The present invention generally relates to the field of interventional guidance of tissue ablation procedures. In particular, the present invention is directed to a system and method for ablation treatment of tissue with interactive guidance.

BACKGROUND

Ablation technologies are used to necrotize tissues for therapeutic purposes. An example of application is treatment of cancer, where ablation is used to treat malignant tissues in order to cure or manage the disease. Another example of application is treatment of arrhythmia, where ablation is used to scar or destroy tissues in the heart that trigger or sustain abnormal heart rhythms.

Various ablation technologies exist, based on different physical principles. Radio Frequency Ablation (RFA) is based on the application of Radio Frequency (RF) energy to the tissues by means of one or multiple contacting electrodes, and on heating up tissues to a temperature high enough to cause tissue necrosis. Microwave Ablation (MWA) is based on the application of Microwave (MW) energy to the tissues by means of one or more contacting antennas, and on heating up tissues to a temperature high enough to cause tissue necrosis.

The above ablation techniques can be applied in minimally invasive fashion. RFA, for example, which is used for treatment of liver, lung, breast and other forms of cancer, can be performed percutaneously, with needle-shaped probes, which are inserted into the tissues through the skin. RFA is also used, for example, in the treatment of arrhythmia, where heart tissues causing arrhythmia are treated with a catheter carrying an RFA electrode. Similarly MWA can be performed percutaneously, for example, in the treatment of liver cancer and other forms of cancer, using needle shaped probes. MWA can also be used, for example, in the treatment of arrhythmia, reaching the target tissues with a catheter.

Ablation may alternatively or additionally be performed using cryoablation. Cryoablation (CRYO) is based on removing heat from the tissues with one or multiple contacting probes, freezing tissues and causing necrosis.

Ablation may alternatively or additionally be performed using irreversible electroporation (IRE). IRE is defined for the purposes of this disclosure, as a non-thermal tumor ablation modality that delivers ultra-short high-voltage electrical impulses to a target volume through contacting electrodes. Resultant strong electric field causes electroporation, or in other words causes permeable nanoscale pores to form in the cell membrane. When the intensity of the induced electric field, as determined by the voltage and duration of the electric pulse, exceeds a particular threshold, the permeable pores on the cell membrane are opened permanently. This causes the membrane to lose its physiological function by preventing it from returning to a state of homeostasis, which in-turn leads to cell apoptosis and the clearing away of cell debris by the host immune system.

In the minimally invasive use of ablation technologies, the operator has no direct view of the tissues that are being treated, as the ablation probe(s) is/are inserted into the body, for example, percutaneously or endoscopically. These procedures are image-guided, where Computed Tomography (CT), Ultrasound (US), Magnetic Resonance Imaging (MRI), Positron Emission Tomography (PET), or Fluoroscopy (FL) images are acquired intraoperatively and used to visualize the tissues and the position of the probe within the body.

In often cases the evaluation of adequacy under image guidance is difficult, as the imaging modality might not be sensitive enough to highlight clearly all the tissues that have been treated, or because the imaging modality might require administration of contrast to the patient for the treated tissues to enhance, but the operator might be limited in the dose of contrast administered, as the contrast might be toxic.

Under image guidance it might be challenging therefore to evaluate whether adequacy has been reached. For example, local recurrence of tumors treated by ablation is largely attributed to procedures that were inadequate, but interpreted as adequate, resulting in certain malignant tissues left untreated.

Systems have been conceived to use computer models to simulate the physics taking place during the ablation to estimate the three-dimensional volume of the ablation, and to display this estimated volume overlaid to patient images as a surrogate of a real image of the treated tissues. However, the computational models used for predicting the ablation volume are computationally expensive.

SUMMARY OF THE DISCLOSURE

In an aspect, a method of modeling a necrotized tissue in an ablation procedure includes providing, at a computational component, a computer model of a volume of human tissue, locating, by the computational component, an ablation site in the computer model, determining, by the computational component, in the context of RFA and MWA, a deposited power density relating to at least an ablation parameter using at least an ablation model, determining, by the computational component, a heat distribution at the ablation site as a function of the deposited power density, and identifying, by the computational component, a volume of tissue necrotized during an ablation procedure performed at the ablation site based on the heat distribution.

In another aspect, and in the context of RFA and MWA, a system for modeling a necrotized tissue volume in an ablation procedure includes a computational component, wherein the computational component is designed and configured to provide a computer model of a volume of human tissue, simulate an ablation site in the computer model, detect, in the computer model, at least a tissue property, wherein the at least tissue property represents at least a physical property of a reference point in the tissue, determine a deposited power density relating to at least an ablation parameter using at least an ablation model, and identify a volume of tissue necrotized by heat during an ablation procedure performed at the ablation site based on the heat distribution.

In another aspect, and in the context of RFA and MWA, a system for simulating an ablation volume includes a computational component, the computational component configured to receive an ablation probe ablative energy data, (or power, or current), calculate an electromagnetic field deposited power density from the ablation probe in a first model ablation volume, calculate, a thermal distribution from the ablation probe in a second model ablation volume, wherein the first model ablation volume is smaller than the second model ablation volume, and determine boundaries of the ablation volume according to the calculations of the electromagnetic field deposited power density and the thermal distribution from the ablation probe in the ablation probe.

In another aspect, a system for determining an ablation footprint of an ablation site includes a computational component, the computational component configured to receive an ablation probe activation energy data (e.g. ablation power and duration in RFA and MWA, cooling temperature and duration in CRYO, or applied voltage and pulse duration in IRE) associated with using an ablation probe at an ablation site, determine an ablation footprint of the ablation probe at the ablation site, wherein determining further includes determining a representation of a necrotic area of the ablation site as a function of the ablation probe activation energy, retrieve a predetermined ablation chart, wherein the predetermined ablation chart includes a predetermined necrotic area as a function of the ablation probe and the energy applied, and generate a display of the ablation footprint and the predetermined ablation chart, wherein the display supports switching between the determined ablation footprint and the predetermined ablation chart.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
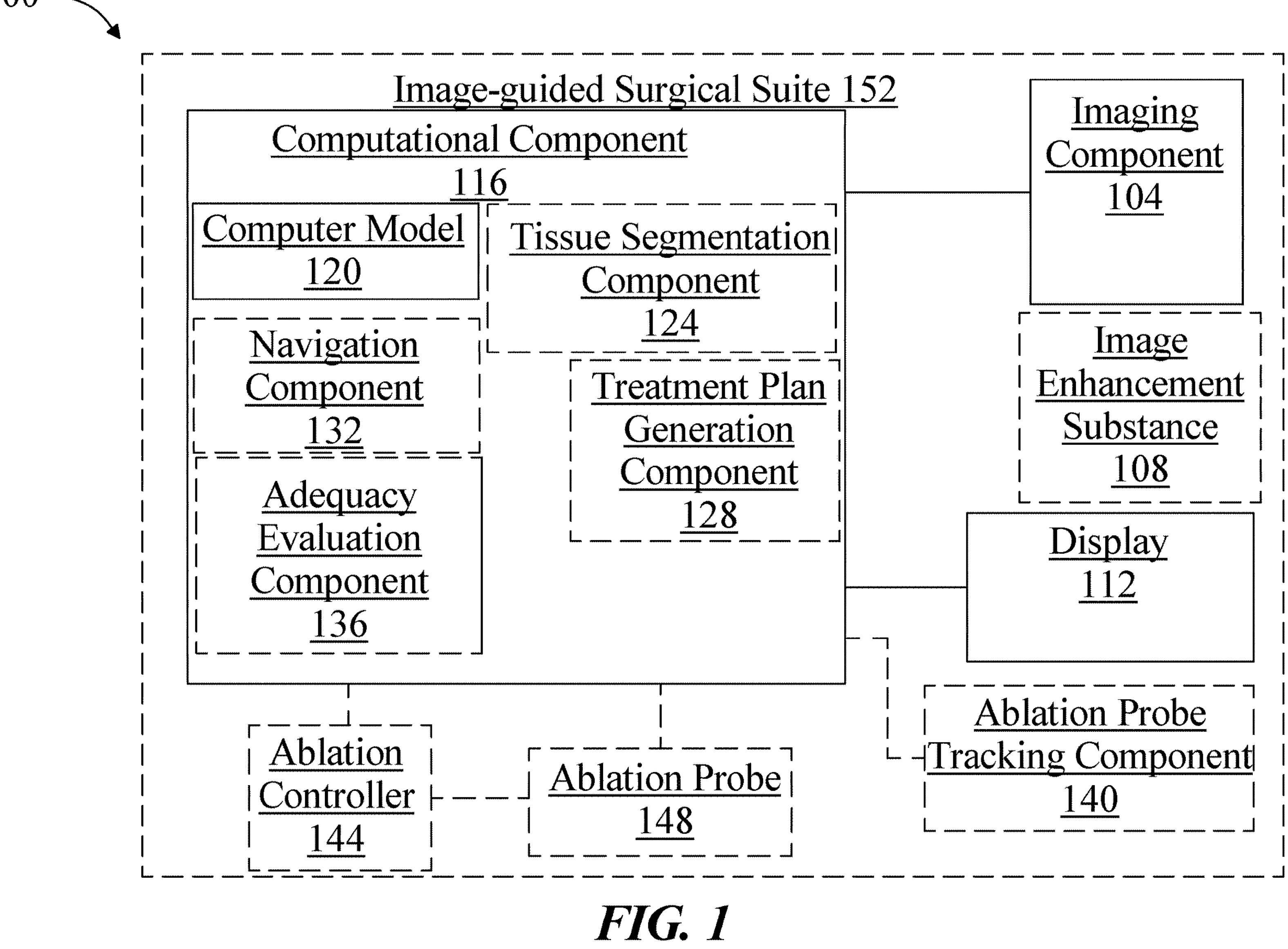
FIG. 1 is a block diagram illustrating an exemplary embodiment of a system for ablation treatment of tissue with interactive guidance.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Methods and systems as disclosed herein generate and display predictive models of ablated tissue and/or ablated volume predictions; such predictions may be generated, in the case of RFA and MWA ablation, by determining a deposited power density relating to at least an ablation parameter using at least an ablation model and determining a heat distribution at the ablation site as a function of the deposited power density. In embodiments, methods and systems as disclosed herein enable generation of visualizations that allow a physician to study which tissues would be treated by a particular ablation probe, energy setting, and position/orientation of the probe inside the body. A physician may be able to use such visualizations to plan an intervention, for example, by determining the single or multiple optimal positions/orientations of the ablation probe inside the body, and levels of applied energy to use, which may result in the complete treatment of the target tissues; complications may be minimized by accurate planning as well. Intraoperative guidance and/or planning according to systems and methods as disclosed herein may be performed in advance, including days in advance, of the procedure in question; alternatively or additionally, intraoperative guidance and/or planning may be performed during a medical procedure such as a percutaneous ablation procedure or a procedure involving percutaneous ablation.

Systems and methods as described herein may be deployed within the context of systems, processes, and procedures for thermal, irreversible electroporation, and/or cryogenic ablation of human or animal tissue. Ablation is a process whereby target tissues such as abnormal or pathological tissues are selectively exposed to heat, cold, radiation, electrical energy, or other phenomena until cell death occurs, causing the abnormal or pathological tissues to die. Thermal ablation is a process whereby abnormal or pathological tissues are selectively heated until cell death occurs, causing the abnormal or pathological tissues to die. Thermal ablation technologies may be used to treat tissues for therapeutic purposes. An example of application may include treatment of cancer, where thermal ablation is used to necrotize malignant tissues in order to cure or manage the disease.

As a non-limiting example a technique for thermal ablation may fall into one of two frequently used categories: Radio Frequency Ablation (RFA) and Microwave Ablation (MWA). RFA is based on the application of Radio Frequency (RF) energy to the tissues by means of one or multiple contacting electrodes. MWA is based on the application of Microwave (MW) energy to the tissues by means of one or multiple contacting antennas. Both technologies cause a local increase in the temperature of tissues which ultimately causes the necrosis of a certain volume of tissues (treatment of tissues). If the volume of treated tissues encompasses all the tissues which are target of the procedure, the treatment is adequate. A single procedure may require multiple overlapping ablations to treat the whole volume of target tissues. Each of RFA and MWA can be applied in a minimally invasive fashion. Both RFA and MWA are, for example, used in percutaneous treatment of liver cancer, where a needle shaped RFA electrode, or MWA antenna, are inserted, through the skin, into the volume of the tumor and used to treat the target tissues.

Ablation may alternatively or additionally be performed using cryoablation. Cryoablation (CRYO) is based on removing heat from the tissues with one or multiple contacting probes, freezing tissues and causing necrosis.

Ablation may alternatively or additionally be performed using irreversible electroporation (IRE). IRE is defined for the purposes of this disclosure, as a non-thermal tumor ablation modality that delivers ultra-short high-voltage electrical impulses to a target area through fine antennae. Resultant strong external electric field causes electroporation, or in other words causes permeable nanoscale pores to form in the cell membrane. When the intensity of the induced electric field as determined by the voltage and duration of the electric pulse exceeds a particular threshold, the permeable pores on the cell membrane are opened permanently. This causes the membrane to lose its physiological function by preventing it from returning to a state of homeostasis, which in-turn leads to cell apoptosis and the clearing away of cell debris by the host immune system.

As a non-limiting example, during RFA, one or multiple electrodes may be inserted into a tumor or lesion to be ablated under guidance of medical imaging, such as ultrasound, computed tomography (CT) or magnetic resonance imaging (MRI). Once the electrodes are placed, a radiofrequency energy may be applied to the electrode creating tissue heating and cell death. In order to destroy tumors that are larger than the volume around the needle tip that is heated and destroyed in a single ablation, the single or multiple electrodes may be repeatedly repositioned to ablate different parts of the tumor, partly overlapping with one another. This process may be repeated until the entire tumor is "covered" by the plurality of ablations, also referred to as the "composite ablation."

In the following the term "ablation probe" or simply "probe" is used to refer devices able to perform the ablation of tissues, such as, but not limited to, RFA electrodes, MWA antennas, CRYO probes and IRE probes. In certain systems multiple ablation probes may be inserted in the tissues and activated at the same time, in order to treat larger volumes of tissues at once.

Referring now to FIG. 1, an exemplary embodiment of a system 100 for ablation treatment of tissue with interactive guidance and/or modeling a necrotized tissue volume in an ablation procedure is illustrated. System 100 may include an imaging component 104. As used in this disclosure an "imaging component" is a device that at least captures images of a particular object and/or entity, such as without limitation images of human tissue, foreign bodies therein, probes, and the like. As a non-limiting example, imaging component 104 may capture the ablation probe 148(*s*) as deployed in the tissues. An imaging component 104 may include, without limitation, a device and/or suite of devices configured to capture and/or manipulate imaging data depicting human tissue; human tissue may be living tissue, including without limitation organ or other corporeal tissue of a prospective subject for an ablation procedure as described in this disclosure. Imaging data may include data describing and/or depicting tissue to be ablated, which may include abnormal and/or pathological tissue, such as tissue containing one or more malignant or benign tumors, lesions, cysts, scar tissue, or the like. Imaging data may include imaging data describing abnormal and/or pathological tissue itself, for instance, image data may describe and/or depict a tumor, lesion, cyst, or the like.

With continued reference to FIG. 1, imaging data may be captured using any technology, device, and/or system for capture of radiological imaging data in two-dimensional or three-dimensional form, or any combination thereof. As a non-limiting example, imaging data may be captured using computed tomography (CT). As a further non-limiting example, imaging data may be captured using X-ray and/or fluoroscopy. As an additional non-limiting example imaging data may be captured using magnetic resonance imaging (MRI). As a further non-limiting example, medical imaging data may be captured using a nuclear medicine scanning technique, such as a technique whereby a radiation, particle, or antiparticle-emitting substance is preferentially absorbed by abnormal and/or pathological tissue, and an image is formed by directly or indirectly capturing output generated by the emitting substance; non-limiting examples include positron-emission tomography (PET) scans. Medical imaging data may, in another non-limiting example, be acquired using photo-acoustic imagery. In an embodiment, and as a non-limiting example, imaging data may be captured using ultrasound technology. Imaging data may, as a further non-limiting example, be captured using optical scanning techniques. Imaging component 104 may include, without limitation, a CT scanner, a C-arm image-acquisition device, an MRI scanner, or an US scanner; persons skilled in the art will be aware, upon reviewing the entirety of this disclosure, of various elements of radiological and/or medical imaging equipment that may be used to capture images. In an embodiment, two or more scanning methodologies and/or technologies may be combined to capture imaging data; for instance, MRI may be combined with CT scanning initially or at different stages in an imaging process and/or procedure. As a further non-limiting example, CT and PET scanning may be combined to generate an image using imaging data captured from tissue. Persons skilled in the art, upon reviewing the entirety of this disclosure, will be aware of various ways in which scanning technology may be used and/or combined to capture imaging data as described in this disclosure.

Still referring to FIG. 1, in an embodiment, capture of imaging data is performed at least in part by introduction of one or more image enhancement substances 108. chemical substances having the property of enhancing the accuracy, contrast, effective resolution, and/or signal to noise ratio of resulting images and/or models of tissue. Such chemical substances, collectively referred to in this disclosure as "image enhancement substances," include without limitation contrast agents such as iodine, barium, gadolinium, or the like, radiopharmaceutical agents that emit particles and/or radiation directly or indirectly, including without limitation agents used in nuclear medicine imaging techniques as described above, fluorescent agents, or the like. Chemical substances may include one or more elements of high-contrast media in liquid, gas, or powder form. Persons skilled in the art, upon reviewing the entirety of this disclosure, will be aware of various forms of chemical substances that may be introduced to tissues to generate, improve, and/or calibrate images captured from the tissues. Chemical substances may be introduced by any suitable means, including without limitation ingestion in liquid or solid form, insertion into one or more orifices such as via enema and/or suppository, injection into tissue, veins, arteries, lymph ducts, and/or interstitial spaces, or insertion using an ablative probe and/or device as described below in further detail. Chemical substances may be paired with, incorporated in, or attached to one or more additional substances or structures aiding in selective absorption by or adhesion to one or more tissues or other anatomical structures of interest; for instance, chemical substances may be paired with, incorporated in, and/or attached to one or more monoclonal antibodies that selectively attach to cellular tissue having particular properties, including without limitation cancerous and/or precancerous tissue, tissue made up of a particular category of specialized cells, or the like.

With continued reference to FIG. 1, capture of imaging data may include capture and/or generation of a three-dimensional image of tissue. Three-dimensional image may be created, without limitation using a combination of a plurality of two-dimensional "slices" captured using imaging technology and/or processes as described above; as a non-limiting example, two-dimensional MRI, CT, or other images of a volume of tissue, such as without limitation an organ or body part, may be combined to generate a three-dimensional image, for instance by capturing a series of two-dimensional images separated by a given resolution space in succession. As a further non-limiting example, a three-dimensional image may be generated by capturing data in the form of a series or plurality of "pixels" and/or "voxels" that are combined to generate a three-dimensional image.

Still referring to FIG. 1, system 100 may include a display 112. As used in this disclosure a "display" is a digital and/or analog representation of a computer-generated image and/or graphic. Display 112 may include, without limitation, a dedicated display 112 attached to a display 112 of the imaging component 104, a computational component 116, a display 112 of an ablation controller 144, a display 112 simply receiving images and computer-generated information from a remotely placed computational component 116, the screen of a laptop, PC, tablet or mobile device able to receive and display 112 images and computer-generated graphics from the computational component 116. Display 112 may display 112 the user guidance information, which includes images, and computer-generated information which guides the user in the procedure, for example the display 112 of estimated ablation volumes overlaid to images of the patient.

Display 112 may generate intraoperative guidance visualizations indicating to a physician or other medical professional a current and/or target location of a probe, implant, scope, or other surgical instrument or item of equipment within a volume of tissue. For instance, and without limitation, display 112 may provide an initial image to a medical professional performing an ablation procedure, the initial image indicating at least an ablation site; indication of at least an ablation site may include indication of one or more areas or locations of abnormal or pathological tissue to be targeted using a probe. Initial image may include a target marker, which may include an added indicator marking an ablation site, such as without limitation an "X" or equivalent marking at a depiction of an ablation site, a circle around the depiction of the ablation site, or the like. Initial image may include a virtual and/or simulated image of a probe as inserted into tissue at the ablation site, which may include depiction of a position and/or orientation of the probe. Initial image may include a plurality of markings and/or virtual and/or simulated images of probes as described above as indicating a plurality of ablation sites; alternatively a plurality of initial images may be generated and/or displayed to indicate a plurality of ablation sites. Initial image and/or plurality of initial images may illustrate and/or depict a boundary surface and/or boundary line within which tissue has been necrotized, including during and/or involving a previous iteration of an embodiment of a method as described in this disclosure, and/or within which tissue is intended to be necrotized in a planned procedure, including without limitation a procedure as guided by processes as described herein. Alternatively or additionally, an image may represent an image generated in a previous iteration of one or more processes and/or process steps as described in this disclosure.

Continuing to refer to FIG. 1, display 112 may provide repeated and/or updated images during probe insertion and/or ablation; for instance display 112 may repeatedly capture and display images, using any imaging technology as described above, of patient tissue and/or probe during probe insertion and/or ablation. Such repeated images may include a continuously updating display 112 such as a video display 112 showing insertion and/or ablation in real time, for instance to indicate to a medical professional a current position and/or orientation of a probe as insertion and/or ablation is taking place, enabling the medical professional to correct a direction and/or angle of insertion and/or to plan a further insertion step; additional images such as elements suitable for use in an initial image as described above may be combined with and/or superimposed on images so displayed, for instance to depict for a medical professional both a target ablation site into which the probe is to be inserted and a current position of the probe during insertion. Imaging and/or modeling systems, methods and technologies, for instance as described herein, may support physicians in evaluating which tissues are to be treated, have been treated, or have not been treated by a particular ablation directly in the operating room, offering a "see-and-treat" functionality.

Still referring to FIG. 1, system 100 may include a computational component 116. As used in this disclosure a "computational component" is electronic equipment controlled by a processor that may compute algorithms. may include any computing device as described in this disclosure, including without limitation a microcontroller, microprocessor, digital signal processor (DSP) and/or system on a chip (SoC), or a Graphic Processing Unit (GPU) as described in this disclosure. Computational component 116 may be housed with, may be incorporated in, or may incorporate one or more sensors of at least a sensor. Computing device may include, be included in, consist of, and/or communicate with a mobile device such as a mobile telephone, smartphone, tablet, or laptop computer. Computational component 116 may include a single computing device operating independently, or may include two or more computing device operating in concert, in parallel, sequentially or the like; two or more computing devices may be included together in a single computing device or in two or more computing devices. Computational component 116 with one or more additional devices as described below in further detail via a network interface device. Network interface device may be utilized for connecting a Computational component 116 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computational component 116 may include but is not limited to, for example, a Computational component 116 or cluster of computing devices in a first location and a second computing device or cluster of computing devices in a second location. Computational component 116 may include one or more computing devices dedicated to data storage, security, distribution of traffic for load balancing, and the like. Computational component 116 may distribute one or more computing tasks as described below across a plurality of computing devices of computing device, which may operate in parallel, in series, redundantly, or in any other manner used for distribution of tasks or memory between computing devices. Computational component 116 may be implemented using a "shared nothing" architecture in which data is cached at the worker, in an embodiment, this may enable scalability of system 100 and/or computing device.

Still referring to FIG. 1, computational component 116 may be designed and/or configured to perform any method, method step, or sequence of method steps in any embodiment described in this disclosure, in any order and with any degree of repetition. For instance, workstation 304 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computational component 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, computational component 116 may provide, store, receive, manipulate, or otherwise work with a computer model 120 of human or animal tissue. Computer model 120 may be used in conjunction with methods and/or method steps as described in further detail below. Computer model 120 may be provided and/or manipulated as described in further detail below.

Computational component 116 may host and run algorithms relating to a tissue segmentation component 124. As used in this disclosure "tissue segmentation component" is a component used to produce segmented images of target tissues of an ablation rendered on display 112. Tissue segmentation component 124 may allow the user to define target tissues of the ablation on images received from imaging component 104, for instance and without limitation using an interaction through a Graphical User Interface (GUI) which is rendered on display 112: alternatively, tissue segmentation may be automatic, requiring no user intervention. Segmentation may be manual, semi-automatic, or fully automatic. Tissue segmentation component 124 may add some margins of the specified thickness to the defined target tissues. Generated margins plus the original targets in this case become together the target of the procedure. Tissue segmentation component may be capable of segmenting other tissues and structures of a body with the aim of using that information for guidance. For example, vessels, if segmented, may be fed to a model to improve prediction of the ablated volume, as vessels may remove heat from the ablation. Other organs may for example be segmented if they should be spared, so that system may indicate if an unsafe situation exists. In an embodiment, tissue segmentation component may be capable of segmenting other tissues and structures of the body; for instance, information determined by segmentation of body structures may be used that information for guidance. For example, images of vessels such as blood vessels, if segmented, can be fed to the model to improve the prediction of the ablated volume, as such vessels remove may remove or deliver heat from ablation site. As a further example, images of other organs may for example be segmented if they should be spared; in this case system 100 may indicate an unsafe situation, which may indicate to a user that one or more probe locations and/or other parameters of ablation should be modified.

Still referring to FIG. 1, computational component 116 may host and run algorithms relating to a treatment plan generation component 128. As used in this disclosure a "treatment plan generation component" is a component relating to a user defined treatment plan. Treatment plan generation component **128*a* may allow the user to define a treatment plan that at least relates to a set of ablation probe 148**(*s*) positions and orientations in space such that, based on the estimated cumulative effect of the probe(s) and of all the ablations conducted with them, the target tissues are treated. Treatment plan generation component 128 may present a navigation component 136 that may guide the user in the insertion and positioning of the probe(s) at the planned positions. As used in this disclosure a "navigation component" is an element of data that relates to the real-time spatial position of the ablation probe 148(*s*) Navigation component 136 may use display 112 to give the user visual information supporting the user in the insertion and placement of the probe(s) according to the established probe(s) spatial positions defining the treatment plan. Treatment plan generation may update the treatment plan while the procedure is ongoing. For example, and without limitation, a lack of a treatment plan may result in the user positioning the probe(s) under standard image guidance procedure and optimizing the fine position of the probe based on the displayed computed ablation volume. As a further non-limiting example, treatment plan generation component 128 may repeat steps described herein for calculation of ablation volume and/or probe placement guidance iteratively or recursively to perform a finer adjustment of the probe placement.

Still referring to FIG. 1, computational component 116 may host and run algorithms relating to an adequacy evaluation component 132. As used in this disclosure an "adequacy evaluation component" is a software or hardware component that provides a visual representation of the target tissues that have already been treated. As a non-limiting example, adequacy evaluation component 132 may highlight in one color, over the patient image, the treated target tissues, and with a second color, the untreated target tissues. Adequacy evaluation component 132 may build an internal map of the tissues that are treated by accumulating the effect of each single ablation, so that the displayed information reflects the overall effect of the procedure up to the current point in time. Adequacy evaluation component 132 may be responsible to display 112 an estimated ablation volume before the ablation is conducted. As a non-limiting example adequacy evaluation component 132 may relate to a user that has not yet activated the probe(s) but is seeking to position it/them optimally based on visual feedback provided. Adequacy evaluation component 132 may display 112 the untreated target tissues in one color, the target tissues already treated in a second color, and the tissues potentially treated by the activation of the probe(s) at the current position in a third color, so that the user can evaluate the effect of an ablation against the tissues that are already treated and against the ones that still need to be treated. Adequacy evaluation component 132 may incorporate numerical models which can simulate the physics taking place during the ablation, producing an estimate of the ablation volume. Adequacy evaluation component 132 in its function may need to have knowledge of the position of the probe(s).

Still referring to FIG. 1, system 100 may include an ablation probe tracking component 140. As used in this disclosure "ablation probe tracking component" is an element that continuously tracks the position of the probe in space. Ablation probe tracking component 140 may allow a navigation component 124 to provide navigation information during the insertion of the probe. As a non-limiting example, ablation probe tracking component 140 may allow the position of the probe to be received by computational component 116 such that the user may insert and position the probe. User may alternatively or additionally insert and place a probe by following standard of care image-guided approaches. Additionally, or alternatively, navigation component 124 may indicate when the tip of the probe is in the proximity of the target tissues, or may provide an indication of an error between a current probe insertion trajectory and a planned one, or a distance between a tip and a planned tip position, as well as indications of how to reduce the distance between the current probe position and the planned probe position. Ablation probe tracking component 140 may be based on electromagnetic or optical methods.

Still referring to FIG. 1, system 100 may include an ablation controller 144. As used in this disclosure "ablation controller" provides energy to the probe in order to ablate the tissues. Ablation controller 144 may provide means for the user to control the ablation settings, as for example, the applied level of power, and the duration of the ablation. Ablation controller 144 may provide information to adequacy evaluation component 132 indicating the status of the tissues, this information may consist of, for example and without limitation, the temperature of the tissues as read from sensors on the probe, or on the impedance of the tissues (in RFA), or in the reflection coefficient at the probe (in MWA). This information may be used by the numerical models present in adequacy evaluation component 132 to better estimate the volume of the ablation. Ablation controller 144 may control and/or regulate supply of energy to a probe, using any suitable energy regulator; where energy supply is electrical and/or may be regulated by electrical parameters such as voltage, current, resistance, or the like, ablation controller 144 may regulate electrical voltage, current, and/or energy level and/or output to probe using any analog and/or voltage regulator and/or control device. For instance, and without limitation, computational component 116 and/or other component of system may command and/or drive ablation controller 144 to commence, cease, and/or vary energy output to a probe according to any process as described below for estimation and/or determination of volumes of ablated and/or necrotized tissue, determining appropriate power levels, ablation locations, and/or duration of power supply at any power level, or the like. Ablation controller 144 may alternatively or additionally be controlled by a user by way of one or more user controls, which may include any manual or other input devices as described in this disclosure, such as without limitation buttons, knobs, keys, a touch pad, a touch screen, a mouse, or the like, where a person operating ablation controller 144 and/or system 100, such as without limitation a physician, may set a level of power applied, a duration of an ablation, and/or start and stop the ablation. Ablation controller 144 may include, a computing device, which may include any device suitable for use as computational component 116 as described above, and/or any other computing device as described in this description; ablation controller 144 may be configured and/or programmed to perform any process step, process, repetitions, and/or iterations thereof that may be performed by computational component 116 as described in this disclosure.

Continuing in reference to FIG. 1, computational component 116 may be configured to receive an ablation probe 148 ablative energy data. Ablation controller 144 may control and/or regulate supply of energy to probe, using any suitable energy regulator; where energy supply is electrical (e.g. RF voltage/current or MW field amplitude) or thermal (e.g. coolant flow rate). The ablation probe 148 applied ablative energy may be used as an input parameter for the ablation volume prediction algorithm in determining to the ablative effect of the probe and simulating an accurate ablation volume.

Still referring to FIG. 1, system 100 may include at least an ablation probe 148. As used in this disclosure "ablation probe" is a surgical tool that applies or removes energy to/from the tissues. As a non-limiting example, ablation probe 148 may be used to apply the energy and ablate the tissues directly. In the context of RFA, a probe may consist of one or multiple electrodes in contact with the tissues, and in the context of MWA a probe may consist of one or multiple antennas able to radiate the microwave energy into the tissues. In the context of CRYO a probe might consist in a tool able to remove heat from the tissues, in the context of IRE a probe might consist in one or multiple electrodes able to apply an electric voltage to tissues. Multiple probes could be used and activated at the same time, to treat a larger volume of tissues.

With continued reference to FIG. 1, computational component 116 may be configured to acquire a confirmation image capturing the position of one or multiple ablation probes 148 in a tissue. A "confirmation image," as used in this disclosure, is an image used to confirm a position of one or multiple probes. A "reference image," defined as an image over which the target tissues will be defined, may also be used in some embodiments. A confirmation image may include an image resulting from any suitable capturing device in a computational component 116. The coordinate system may be defined using reference image, and may be used as a spatial reference. Image manipulation and processing may be performed, without limitation, by imaging component.

Still referring to FIG. 1, computational component 116 may be configured to simulate the ablation volume using a "an ablation simulation algorithm" as used in this disclosure, is a software program encapsulating the mathematics and physics outlined herein to simulate the ablation volume. The ablation volume may be computed using models that reflect the physics of the ablation, as described in further detail below. In the context of RFA and MWA, simulating, by the ablation simulation algorithm includes calculating an ablation volume about the ablation probe 148 in the tissue by calculating power deposition from the ablation probe 148 in a first model ablation volume. This first model ablation volume may then be used as an input for calculating, a thermal distribution from the ablation probe 148 in a second model ablation volume, wherein the first model ablation volume is smaller than the second model ablation volume. The smaller first model ablation volume may confer specific computation advantages, such as reducing the computational expense of real-time ablation volume calculation, faster simulation output, and the like.

Further referring to FIG. 1, and as a non-limiting example, computational component 116 may simulate the ablation volume, in the context of RFA and MWA, as a function of calculating an ablation volume about the ablation probe 148 in the tissue, wherein calculating includes calculating a deposited power density (DPD) from the ablation probe 148 in a first model ablation volume. Deposited power density from the ablation probe 148 may result in a determined model (simulations), which are described by Partial Differential Equations (PDEs) and by their boundary conditions, as discretized in implementations herein (with no loss of generality) using the Finite Element Methods (FEM) in the spatial domain and using the Finite Difference Method in the temporal domain, as described below. Deposited power density may be simulated in a first model ablation volume about the ablation probe 148 in a biological tissue. This first model ablation volume may be used as an input model (simulation) for determining the thermal distribution resulting from the ablation probe 148.

Continuing in reference to FIG. 1, in the context of RFA and MWA, system 100 may calculate a thermal distribution from the ablation probe 148 in a second model ablation volume, wherein the first model ablation volume is smaller than the second model ablation volume. The first model ablation volume may include a simulated volume that is "smaller," which as used in this disclosure, is a geometrically smaller volume. Calculating a thermal distribution from the ablation probe 148 in a second model ablation volume, wherein the first model deposited power density may save computation by calculating DPD over a smaller volume (due to decay) and applying results therefrom for a larger thermal volume (thermal distribution). This may simplify, and therefore speed up, calculations of the image processing algorithm without losing accuracy. The boundaries of the first model ablation volume may include a different footprint than second model ablation volume. Thermal distribution resulting from the ablation probe 148 may result in a determined model (simulations), which are described by Partial Differential Equations (PDEs) and by their boundary conditions, as discretized in implementations herein (with no loss of generality) using the Finite Element Methods (FEM) in the spatial domain and using the Finite Difference Method in the temporal domain, as described below.

Continuing in reference to FIG. 1, determination of an ablation footprint and/or volume of the ablation probe 148 at the ablation site, may include determination of a necrotic area of the ablation site as a function of the ablation probe 148 ablation energy and/or a representation thereof. Computational component 116 may determine an ablation footprint using an ablation simulation algorithm, wherein an ablation simulation algorithm is a software program encapsulating the mathematics and physics outlined herein to simulate the ablation volume, as described above. The ablation volume may be computed using models that reflect the physics of the ablation, as described in further detail below. Simulating, by the ablation simulation algorithm includes calculating an ablation volume about the ablation probe 148 in the tissue by calculating, in the context of RFA and MWA, a deposited power density (PDP) from the ablation probe 148 in a first model ablation volume. This first model ablation volume may then be used as an input for calculating, a thermal distribution from the ablation probe 148 in a second model ablation volume, wherein the first model ablation volume is smaller than the second model ablation volume. The smaller first model ablation volume may confer specific computation advantages, such as reducing the computational expense of real-time ablation volume calculation, faster simulation output, and the like.

Alternatively or additionally, speed and/or accuracy of ablation volume prediction and/or detection may be improved by retrieval of one or more stored values representing, e.g., likely deposited power density, temperature, field strength, or other parameters of ablative procedures at given distances from probe given known parameters; such values may be stored and/or retrieved from a look-up table as described in further detail below.

Continuing in reference to FIG. 1, computational component 116 may be configured to retrieve a predetermined ablation chart, wherein the predetermined ablation chart includes a predetermined necrotic area as a function of the ablation probe 148 and energy applied, duration of ablation, or other parameters that affect ablation volume. A "predetermined ablation chart," as used in this disclosure, is any predetermined data concerning the ablation footprint of an ablation probe 148. A predetermined ablation chart may include a "kill chart," which includes predetermined values, such as developed by the ablation probe 148 manufacturer, which describes predetermined distances for varying degrees of necrosis according to the supplied energy to the probe and the probe's specifications. As described above, the ablation footprint is a distribution of ablation effect over a distance, which may describe the expected degree of necrosis. Ablation footprint distribution may include a geometric space, such as a surface area, or volume. Such an ablation footprint may include a "kill chart," for instance a distance about the probe surface around which an expected amount of necrosis may occur. Computational component 116 may retrieve any type of predetermined ablation chart, such as a table of values retrieved from a database, supplied with a software program alongside the ablation probe 148 or the like Continuing in reference to FIG. 1, computational component 116 may be configured to generate a display 112 of the ablation footprint and the predetermined ablation chart, wherein the display 112 supports switching between the determined ablation footprint and the predetermined ablation chart. "Switching," as used in this disclosure, is any form of toggling, comparing, or otherwise accommodating switching between options; switching may be performed within a display 112 by pressing a single key, making a single choice from a menu, or the like Switching may include a split-screen comparison on a display 112 that may inform an in individual, such as a physician, to the degree of the calculated ablation footprint and the manufacturer's "kill chart". Toggling displays 112, information, or the like, may include real-time models (simulations) of the ablation footprint being compared to certain values retrieved from a predetermined ablation chart, for instance as stored and/or retrieved in a database.

Alternatively or additionally, display 112 may be configured not only to switch between a kill chart and a calculated footprint, but to switch between any two representations of currently killed tissues or potentially killed tissues, such as currently or potentially killed tissues which may produced by a cumulative effect of multiple single ablations. In the case of kill charts, cumulative ablation volumes from multiple ablations may be computed as a union of all such volumes, while in the case of simulations, aggregate or cumulative volumes may be computed using any suitable model that may occur to persons skilled in the art upon reviewing the entirety of this disclosure. At any point a physician and/or other medical professional may be able to switch display 112 between a representation of cumulative effects computed from kill charts and a representation thereof from simulations.

Figure 2:
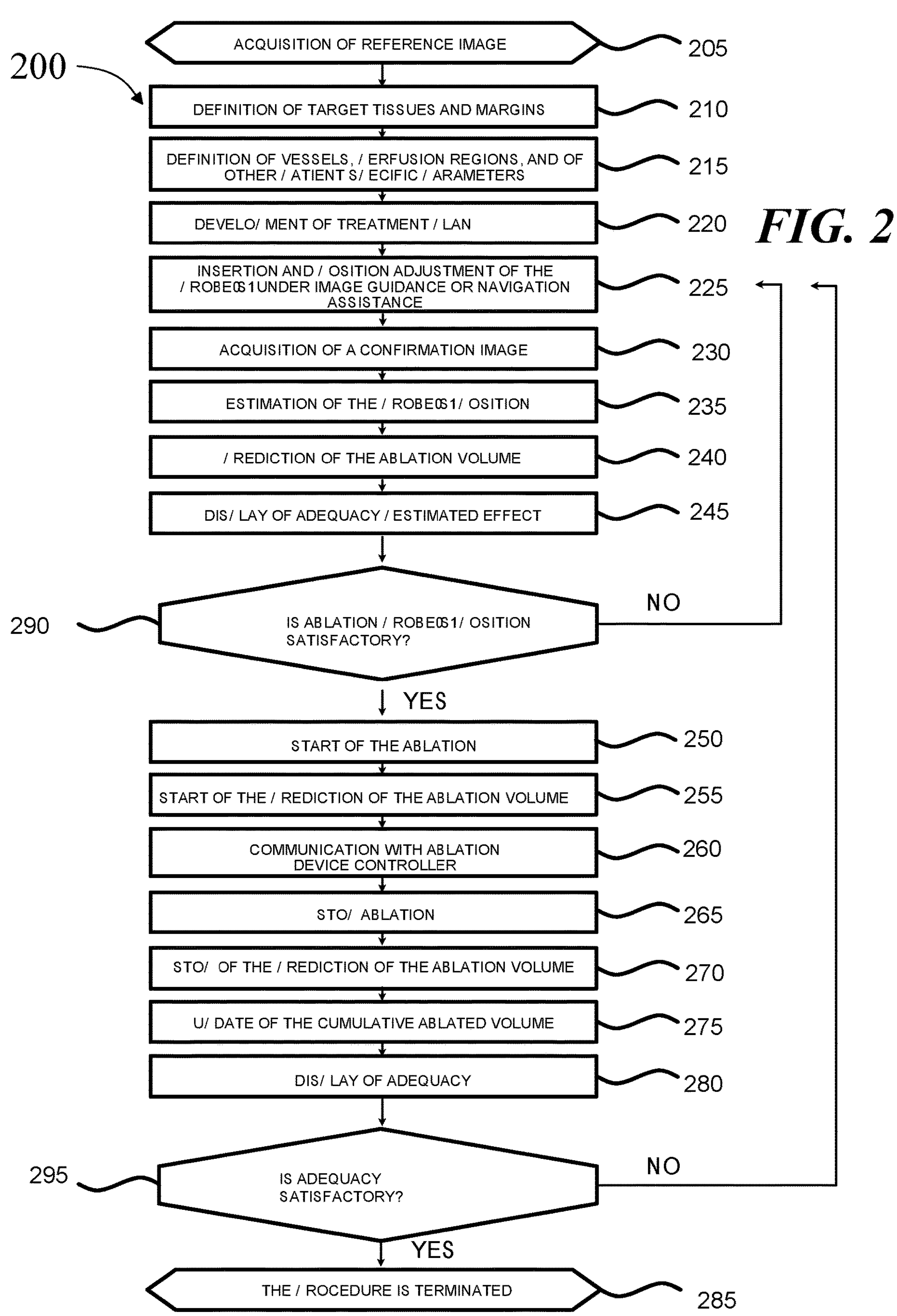
FIG. 2 is a flow diagram illustrating an exemplary embodiment of a method for ablation treatment of tissue with interactive guidance.

Now referring to FIG. 2, an exemplary embodiment 200 of a method of modeling a necrotized tissue volume in an ablation procedure is illustrated. At step 205, an initial reference image over which the target tissues will be defined is acquired. The coordinate system defined by this reference image will be used the spatial reference.

Still referring to FIG. 2, at step 210, a system 100 uses tissue segmentation component 124 such that the user defines the target tissues and margins, the margins are to be considered also target tissues. Tissue segmentation component 124 may include any of the tissue segmentation component 124 as described above, in reference to FIG. 1.

Still referring to FIG. 2, at step 215, system 100 may instruct the user to optionally use tissue segmentation component 124 to segment other body structures like vessels or particular regions of tissues and assign properties, wherein properties may include electrical and/or thermal properties, to these structures or regions of tissues which would be later utilized by the numerical models predicting the ablation volume.

Still referring to FIG. 2, at step 220, system 100 may develop a treatment plan consisting of a set of probe(s) positions in space and ablation parameters, wherein parameters may include applied power and/or duration of power, can be optionally defined by the user using treatment plan generation component 128. Treatment plan generation may include any of the treatment plan generation as described above, in reference to FIG. 1.

Still referring to FIG. 2, at step 225, system 100 instructs the user to insert ablation probe 148(*s*)140 into the body and advance the tip reaching the target tissues, or a location nearby, using standard of care image-guided approaches, or indications from navigation component 136. Ablation probe 148 may include any of the ablation probe 148 as described above, in reference to FIG. 1. Navigation component 136 may include any of the navigation component 136 as described above, in reference to FIG. 1. Alternatively or additionally, a user may enter an instruction on system indicating that the user is going to insert a probe.

Still referring to FIG. 2, at step 230, system 100 may instruct a user, or wait for a user, to use the imaging component 104 to acquire a confirmation image capturing the position of the probe(s) in the tissues. Imaging component 104 may include any of the imaging component 104 as described above, in reference to FIG. 1.

Still referring to FIG. 2, at step 235, system 100 estimates the probe position using adequacy evaluation component 132, wherein adequacy evaluation component 132 may use automatic or semi-automatic image processing algorithms to identify the position of the probe in the confirmation image and/or use image registration algorithms to refer the probe(s) position(s) to the reference image coordinates. Adequacy evaluation component 132 may include any of the adequacy evaluation component 132 as described above, in reference to FIG. 1.

Still referring to FIG. 2, at step 240, adequacy evaluation component 132 may use numerical models, such as without limitation model 120, to predict the ablation volume resulting from the activation of the probe(s) and may highlight it, together with the target tissues, over the reference image, permitting to evaluate the effect of the ablation against the target tissues. In order to estimate the ablation volume in a sufficiently short time, advantageous approaches to this simulation, as described later in detail, are utilized.

Still referring to FIG. 2, at step 245, system 100 instructs the user to evaluate whether the position of the probe(s) is optimal. For example, and without limitation, should the probe(s) not be located in the optimal position the user will reposition the probe(s) under image guidance approaches as described above in reference to steps 225-240. As a further non-limiting example, should the probe(s) be located in the optimal position, the user will proceed to step 250.

Still referring to FIG. 2, at step 250, system 100 starts the ablation by instructing the user to operate the ablation controller 144 in order to start the ablation. Ablation controller 144 may include any of the ablation controller 144 as described above, in reference to FIG. 1. Computational component may alternatively or additionally be interfaced with and/or in communication with ablation controller; for instance, in some embodiments, user may be able to start ablation, upon which event system may detect commencement and proceed to a subsequent step.

Still referring to FIG. 2, at step 255, system 100 simulates the ablation volume within adequacy evaluation component 132. In order to estimate the ablation volume in a sufficiently short time, advantageous approaches to this simulation, as described later in detail, may be utilized.

Still referring to FIG. 2, at step 260, adequacy evaluation component 132 communicates with the ablation controller 144 in order to receive information about the ablation parameters and/or the status of the tissues. As a non-limiting example, information can be used to track changes in the ablation or tissues and to improve the prediction of the ablated volume. Adequacy evaluation component may communicate with ablation controller; alternatively adequacy evaluation component may prompt a user to provide parameters characterizing the energy of an ablation such as applied power and duration, or the status of tissues such temperature, for instance by entering them for example on the display.

Still referring to FIG. 2, at step 265, system 100 may instruct the user to terminate the ablation according to the use guidelines of ablation controller 144. Alternatively or additionally, user may terminate ablation, and either user may enter an instruction indicating termination to system 100 or the system may automatically determine that termination has occurred by receiving a signal from ablation controller.

Still referring to FIG. 2, at step 270, system 100 may instruct and/or permit the user to confirm, for instance through a GUI produced by adequacy evaluation component 132 on display 112, that the ablation has been terminated, that a user instruction to terminate ablation has been executed, or the like. Display 112 may include any display 112 as described above in reference to FIG. 1. Additionally or alternatively, when adequacy evaluation component 132 is in communication with ablation controller 144, adequacy evaluation component 132 may determine that the ablation has been terminated. At this point the simulation run within adequacy evaluation component 132 will be terminated.

Still referring to FIG. 2, at step 275, system 100 updates of the cumulative ablated volume. As a non-limiting example system 100 may identify a final estimated ablation volume as a "tissue damage map" where a tissue damage map is a map recording which tissues have been ablated. The tissue damage map will accumulate the effect of the last ablation by marking the tissues within the estimated ablation volume resulting from the simulation at as treated, or, for example, by updating a numerical value representing the current degree of necrotization for the tissue. Numerical value may include a number, for instance on a range from 0 (no damage) and 1 (full necrotization) which is updated; some tissues may reach, for example, a necrotization value of 0.5 from a first ablation while a second ablation may bring them to 1.

Still referring to FIG. 2, at step 280, adequacy evaluation component 132 may present on display 112 the patient images overlaid with a representation of the ablated tissues which will help the user to understand whether accuracy has been achieved. For example and without limitation, by highlighting the untreated target tissues in one color, and the treated target tissues in a second color, wherein the second color is different from the first color. The highlighting of any untreated tissues will indicate visually that the adequacy has not been achieved.

Still referring to FIG. 2, at step 285, system 100 signals that the procedure can be terminated due to adequacy being achieved. As a non-limiting example when adequacy has been achieved and the clinical goal has been obtained the workflow will terminate. Additionally or alternatively, should adequacy not be achieved the user will perform more ablations, reducing the volume of untreated target tissues until adequacy has been achieved. A user may also decide to terminate procedure without achieving adequacy, for example if it would be too risky to necrotize certain tissues close to certain organs or body structures that cannot be damaged Referring now to FIG. 3, an exemplary embodiment of a method 300 of modeling a necrotized tissue in an ablation procedure is illustrated. At step 305, method 300 includes providing, at a computational component, a computer model 120 of a volume of human tissue. Computer model 120 may include any graphical computer model 120 suitable for depiction of tissue, including without limitation organ tissue or regions of corporeal tissue in which an ablation procedure is to be performed, abnormal and/or pathological tissue to be removed, and/or a site or sites for location of ablative probes, and/or any graphical computer model 120 suitable for planning and/or guidance of procedures such as image-guided surgical procedures and/or ablative procedures as described in this disclosure, and/or any other use in systems and/or methods for medical imaging, planning of procedures, and/or image-guided medical procedures as may occur to a person skilled in the art upon reviewing the entirety of this disclosure. Computer model 120 may include one or more two-dimensional images and/or views and/or one or more three-dimensional images; two-dimensional and/or three-dimensional images may include a plurality of pixels, voxels, vector values, polygons, geometric primitives, or other data elements used to track, render, and/or depict two and/or three-dimensional images. One or more two and/or three-dimensional images may include component images; for instance, a three-dimensional image may include an assembly, collection, and/or plurality of two-dimensional images, such as "slices" as captured in imaging processes as described in this disclosure, which combine to create a three-dimensional image. Computer model 120 and/or computational component 116 may be configured to generate and/or display a plurality of views, or displayed images based on the computer model 120, of the computer model 120 to a user, for instance in response to one or more user commands to modify a view angle and/or magnification of a displayed image generated from and/or using computer model 120; as a non-limiting example, a user may be able to rotate, pan, and/or zoom into or out of an image displayed based on computer model 120. As a further non-limiting example, user may be able to change a contrast level, color scheme, or displayed layer of computer model 120 as illustrated in a view. Where, for instance, computer model 120 is created by combination of image data captured using two or more medical imaging techniques, user may be able to modify view to show only one imaging technique; this may, for instance, enable user to view an image that emphasizes an area of abnormal and/or pathological tissue, and/or one or more organs or other identifiable anatomical features. Computer model 120 may be generated according to any process, process step, and/or combination of process steps that may occur to persons skilled in the art, upon reviewing the entirety of this disclosure, for generation of a computer model 120. Computer model 120 may include, without limitation, an anatomical model, which may include without limitation tumors, veins, arteries, and/or other anatomical structures; for instance, and without limitation, computer model 120 of a liver may include a detailed anatomical model of the patient's liver parenchyma, tumors, hepatic vein, portal vein, and/or arteries.

Figure 3:
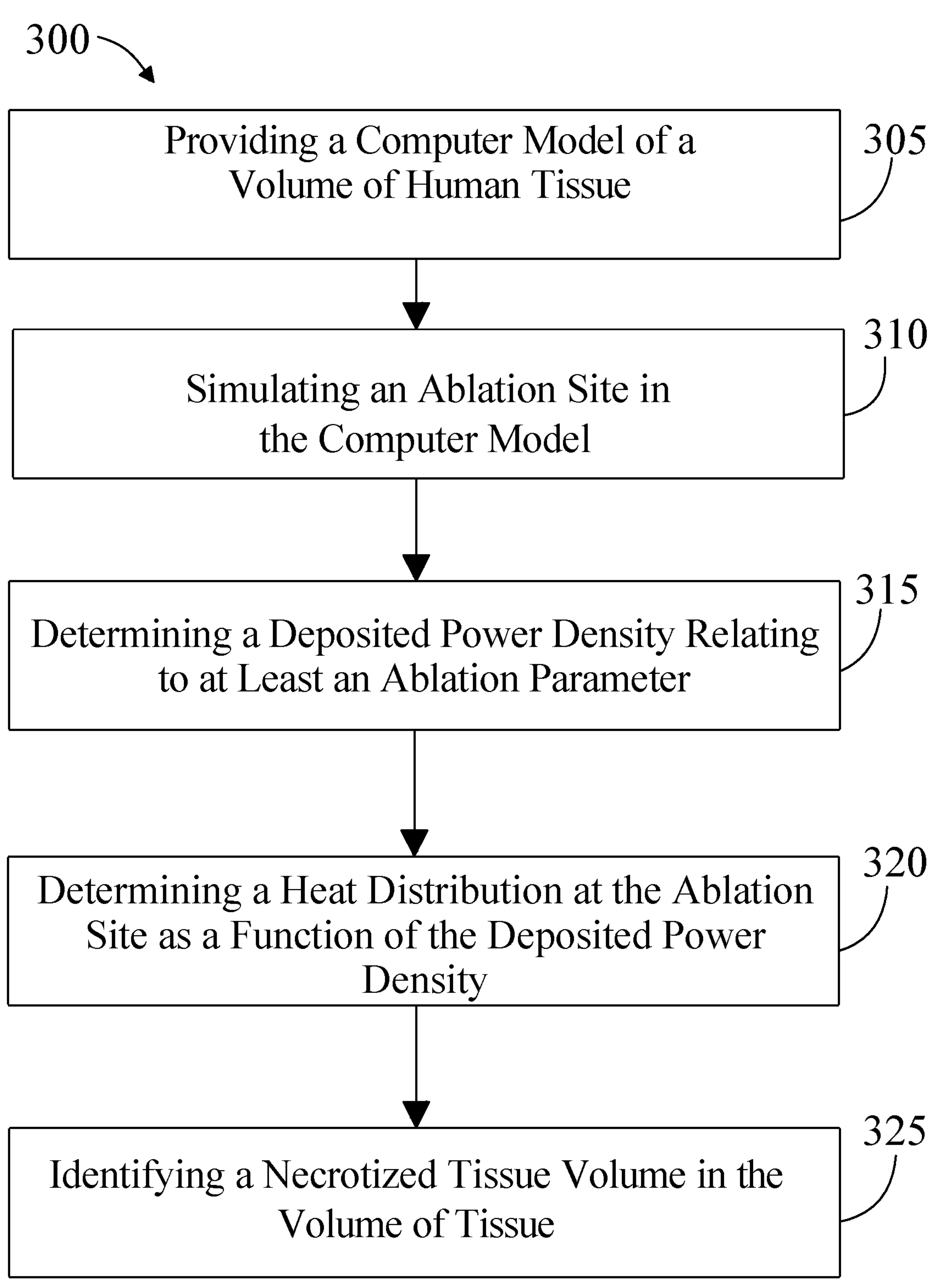
FIG. 3 is a flow diagram illustrating an exemplary embodiment of a method for modeling a necrotized tissue volume in an ablation procedure.

Still referring to FIG. 3, computational component 116 may generate computer model 120. Generation of computer model 120 may include reception and/or capture of one or more images of human tissue from and/or using an imaging component 104. For instance, a three-dimensional surface and/or volume of an area of tissue, organ, or the like may be generated by a process of automatic or semi-automatic segmentation from two- or three-dimensional medical data; this may be performed, without limitation, using segmentation component 116. As a non-limiting example, a user may define seeds inside and outside each area of interest, such as parenchyma, tumors, hepatic vein, portal vein, and/or arteries in image data depicting a liver; an algorithm may subsequently automatically estimate and/or detect a boundary of a structure and/or area of interest. Algorithm to automatically estimate and/or detect a boundary of a structure and/or area of interest may include, without limitation, a random walker algorithm. Algorithm to estimate and/or detect a boundary may include, without limitation, a region growing algorithm. As a further non-limiting example, algorithm to estimate and/or detect a boundary may include, without limitation, a level set algorithm, or alternatively an AI-based algorithm. Alternatively or additionally, a plurality of data entries describing past procedures may be used as training data, which may include any training data as described in further detail below, for instance correlating images with identifications entered by users or other systems and/or processes of boundaries, one or more pixels, voxels, and/or coordinates contained in and/or located at boundaries, or the like; boundary detection may be performed using any form of machine learning and/or deep learning as described in further detail below, including without limitation lazy learning, neural net processes, and/or generation of one or more machine-learning models. Such boundary identifications may be modified and/or improved by further user entries; for instance, a user may identify a point that an algorithm identified as within a structure and/or area of interest as outside the structure and/or area of interest, causing the algorithm to regenerate a boundary using the modified and/or additional information furnished by such an identification. Further continuing the non-limiting example, resulting segmentations may be combined and/or merged into a multi-label mask image, which may be used to generate a model made up of pixels, voxels, vector values, and/or geometric primitives, such as without limitation a triangulated surface or a tetrahedral multi-domain mesh. Such generated images may be overlaid on and/or combined with images captured from user data, including without limitation CT scans, MRI scans, or the like.

Continuing to refer to FIG. 3, virtual model may be generated using image segmentation techniques to capture geometry of organs and/or important structures or regions of interest, including for instance the boundary of a liver, venous and arterial vascular trees, malignant tissues, and/or other organs and/or structures not involved in an intended ablation; such organs and/or important structures may include structures for which having a model and/or a 3D visualization may involve navigation of the surgical tools of the planning for optimal entry points, such as entry points that evade structures such as ribs, spine, lungs, and/or a gallbladder, which may either block or be damaged by a probe or other item inserted into a user's body. Identification of such structures may involve performance of a number of registration algorithms, such as without limitation algorithms, such as segmentation algorithms, based on region growing mechanisms, level set methods, graph cut methods, and/or based on Artificial Intelligence and/or Deep Learning approaches. A machine learning process may include any of the machine learning process as described below such as a process that automatedly uses a body of data known as "training data" and/or a "training set" to generate an algorithm that will be performed by a computational component/module to produce outputs given data provided as inputs; this is in contrast to a non-machine learning software program where the commands to be executed are determined in advance by a user and written in a programming language. Generating computer model may include generating the computer model from an image of the volume of human tissue. Generating computer model may include registering a virtual model of a tissue over an image of volume of human tissue, where the registered virtual model is taken as a model of the specific patient and used to simulate the ablation and estimate the ablation volume in a patient-specific fashion. Computer model may include at least a microwave field propagation model. Computer model may include at least a radiofrequency field propagation model. Computer model may include a computational electromagnetics model, or models able to describe the physics of CRYO or of IRE At step 310, and still referring to FIG. 3, method 300 includes locating, by the computational component, an ablation site and/or probe in the computer model. Location of ablation site and/or probe may be performed, without limitation, using tracking component 140 and/or via image processing. In an embodiment, locating an ablation site and/or probe may include identifying and/or marking one or more areas and/or elements of pathological and/or abnormal tissue, for instance as described above. Probe and/or ablation site location may be performed, without limitation, by a tracking subsystem and/or imaging algorithm. A user may enter a command selecting the one or more areas and/or elements, for instance using a mouse, touchscreen, or other input device. A user may, for instance, "click" on, circle, mark, or otherwise delimit or indicate a location in the tissue depicted or modeled by computer model 120 as a location of abnormal and/or pathological tissue to be ablated. Simulation of an ablation site and/or probe location in computer model 120 may include identification of an area or volume of tissue to be necrotized, such as an area or volume containing abnormal and/or pathological tissue. A user may identify such an area or volume, for instance by drawing a line or series of lines around an area the user has identified for ablation; alternatively or additionally, computational component 116 may generate a curve, volume, and/or surface representing a typical shape of tissue ablated using an ablative probe, which user may rotate, resize, and/or otherwise manipulate to encompass tissues the user has selected for ablation and/or probe location. A user may input a spatial extent of an ablation probe 148, a type of ablation, a duration of ablation, a desired dose, an indication of a spatial extent of a tumor or other area or element of abnormal and/or pathological tissue, an indication of a location in the area or element of abnormal and/or pathological tissue, an amount of power for ablation, a type of ablation device, a sequence of power, and/or other characteristic of the ablation or tissue. Various inputs may be automated. Instead of user input, computational component 116 may provide any of the above information. Computational component 116 may modify variables linked to a size and/or shape of ablated tissue; for instance, where a user enters a command and/or indication that a larger area of tissue is to be ablated, computational component 116 may modify a variable describing a type or size of probe to perform the ablation, a variable describing time and/or intensity of an ablative procedure, or the like. A user may have access to a discrete number of ablation probes 148, such as without limitation RF electrodes with diameters of 2 cm, 3 cm 4 cm. A user may, for instance in MW systems, have an option to select power from a finite number of power-level options and/or durations for which each power level may be employed; as a non-limiting example presented for illustrative purposes only, a user may enter instructions selecting power levels of 60 W, 100 W, 140 W to be deployed for 40 s, 60 s, and 80 s, respectively. Location of a probe and/or ablation site may be performed multiple times sequentially and/or in parallel; for instance, multiple probe locations may be determined for a single ablation site or set of ablation sites.

Still referring to FIG. 3, a model of an ablation site may further incorporate geometry of the ablation probe 148 as deployed in the tissues. An ablation probe 148 may be composed at list partially of flexible parts, such as without limitation tines in RF probes; these parts may be subject to deformation when deployed in the tissues, which may result in the final geometry of the deployed device differing from the original geometry of the device. Algorithms may be used for identifying and/or predicting a true geometry of a device as inserted to generate models of an ablation site which incorporate the true geometry of the deployed device or devices. Imaging sequences may be used to gather information about tissue parameters which affect ablation. For example, and without limitation, CT or MRI perfusion imaging sequences may be used to estimate perfusion point by point in the tissues, and this information can be incorporated into the model. Additionally parameters like the amount of fat and water per unit of volume may be imaged and incorporated into virtual model.

Still referring to FIG. 3, additional parameters that a computational component 116 may modify, select, model, and/or use as inputs to any process described herein may include electrode size, for instance for RFA processes where tines may be deployed to generate an umbrella and this umbrella has a given diameter, power and duration of ablations, for instance for MW, where an ablation probe 148 may look like a straight needle, and the user may change the applied power and the duration, a degree to which RF tines are extended into tissue, e.g. for a probe with slidably retractable tines, or the like. User and/or automated inputs may include a selection of at least a probe model, a selection of at least a power level, a selection of at least a duration of power to be supplied, and/or a selection of a number of overall ablations to be performed in a procedure.

As a further non-limiting example, and continuing to refer to FIG. 3, computational component 116 may modify an identified probe location and/or orientation as described below, in response to user commands modifying a shape or volume of tissue to be necrotized. Alternatively or additionally, computational component 116 may split an area to be necrotized, as identified and/or modified as described above, into two or more simulated ablation sites as described in further detail below. In an alternative embodiment, a user may not indicate placement. Instead, the position may be selected automatically based on the image data, such as by identifying a center of a tumor and/or an identified area and/or element of abnormal or pathological tissue. Various possible placements may be automatically identified and tested with separate simulations. In an embodiment, computational component 116 and/or another component of system 100 may generate a prediction and/or simulation of an ablation volume or other result of ablative process as a function of and/or based on ablation parameters such as without limitation ablation energy data, probe location, numbers of probes, locations and/or properties of tissues at or near ablation site, and the like.

Still referring to FIG. 3, computational component 116 may simulate a plurality of ablation sites. For instance, a user may indicate a sequence of placements for locating sequential ablation operations or applications; such a sequence is simulated by repeating any step or steps as described in this disclosure for simulation of an ablation site, in any order or degree of repetition, for each sequential probe position. Simulation of multiple ablation sites may be performed iteratively, for instance using results from a first simulated ablation site to simulate a second ablation site. Using modeling of tissue and/or cellular necrosis as described in further detail in this disclosure, modified tissue properties for various locations may be considered during the subsequent simulations. Sequential placement may be used for larger tumors, where the single probe placement does not provide sufficient coverage of the ablated tissues volume to the tumor. In another possible implementation, a user may indicate multiple placements for locating ablation using multiple devices at a same time; an aggregate thermal dose may be computed using a combination of individual thermal doses.

Still referring to FIG. 3, computational component may determine at least a field propagation through tissue volumes. Field propagation may include at least a Radio Frequency Ablation (RFA) model, a Microwave Ablation (MWA) model, a cryogenic model, and/or an IRE model. The models, which are described by Partial Differential Equations (PDEs) and by their boundary conditions, may be discretized in our implementation (with no loss of generality) using the Finite Element Methods (FEM) in the spatial domain, and using the Finite Difference Method in the temporal domain.

Figure 4:
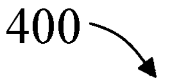
FIG. 4 is a flow diagram illustrating an exemplary embodiment of a method of modeling a necrotized tissue volume in an ablation procedure.
Figure 4:
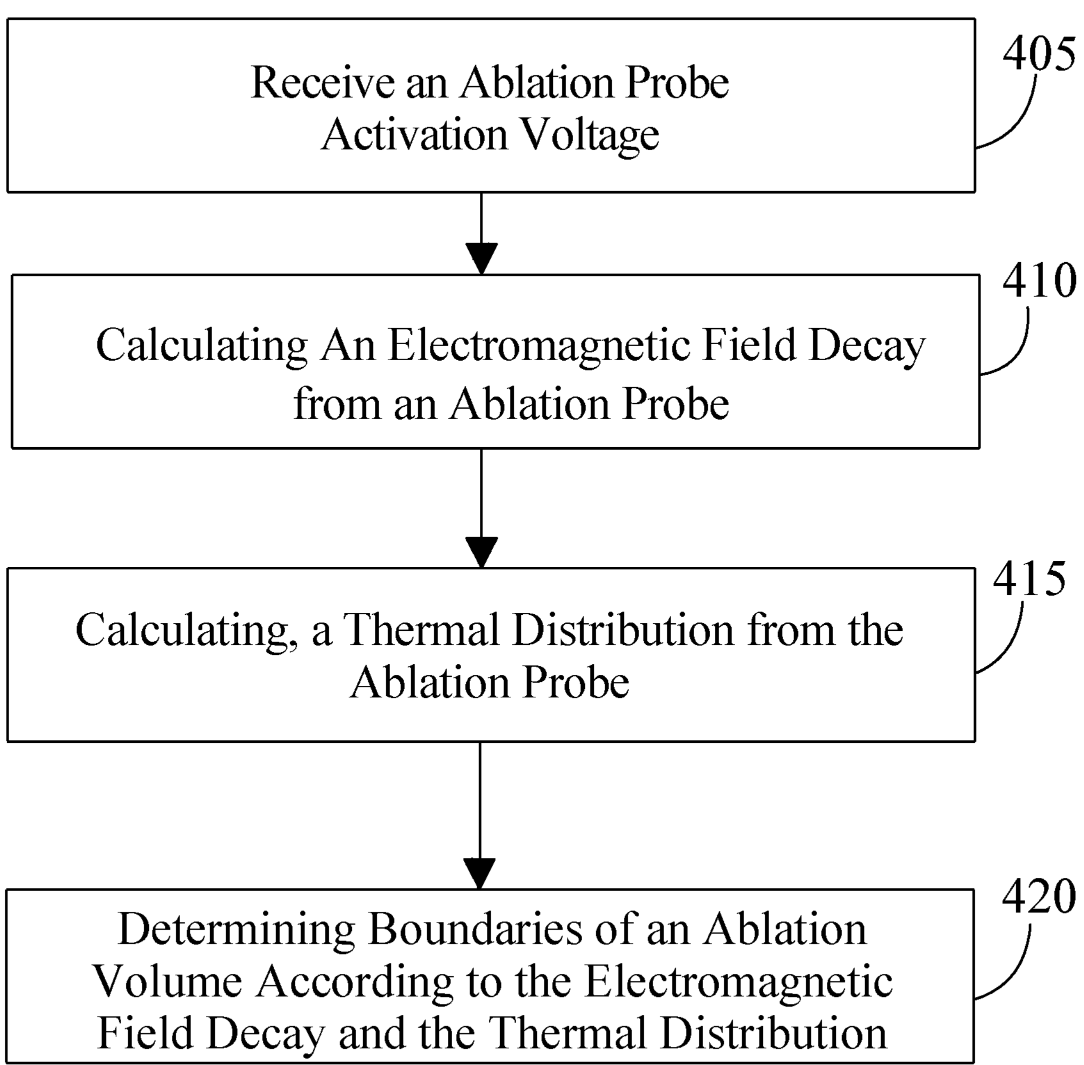

In an embodiment and still referring to FIG. 4, system 100 may simulate the physics of RFA. The RFA thermal field can be described, for example, by the Pennes bioheat equation:

$$\rho C\frac{\partial T}{\partial t} = \nabla\cdot k\nabla T + Q_{RF} + Q_B \tag{0.1}$$

where ρ is the density of the tissue, C is the specific heat capacity, T is the temperature, t is time, k is the thermal conductivity of tissues, $Q_{RF}$ is the electrical power density deposited by the application of RF energy, $Q_B$ is a term that models any biological source or sink of heat (like the heat sink effect of vessels and perfusion). Equation (0.1) allows to compute the evolution of temperatures at the ablation site when the input parameters are specified. The parameters ρ, C are functions of the tissues, as is $Q_B$, $Q_{RF}$ depends instead on the applied RF energy, and can be calculated using the Laplace equation:

$$\nabla\cdot\sigma\nabla u = 0 \tag{0.2}$$

where σ is the electrical conductivity of tissues and u is the electrical potential that develops in the tissues under the effect of the ablation probes 148. The multiple ablation probes 148 are described with boundary condition:

$$V_l = u + zc_l\sigma\frac{\partial u}{\partial\hat{n}} \tag{0.3}$$

where $V_l$ is the voltage applied to the l-th probe, with l=1 . . . L where L is the number of probes, $zc_l$ is the contact impedance of the l-th probe, and $\hat{n}$ is the normal to the surface of the probe. Solving equation (0.2) for u allows to compute $Q_{RF}=\sigma\nabla u\cdot\nabla u$ Equations (0.1), (0.2), and (0.3) are discretized spatially with the Finite Element Method and temporally with the Finite Difference Method resulting in the estimation of the temperatures T at the ablation site and over the duration of the ablation. The computed temperatures are fed into a tissue damage model to determine which tissues will be necrotized, and hence the ablation volume. The tissue damage may be modeled, without limitation, with the Arrhenius equation:

$$\Omega = \int_{t_S}^{t_F} A e^{\frac{-E_a}{RT(t)}} dt \tag{0.4}$$

where $\Omega$ is the tissue damage, a function of space which takes a value of 0 where no tissues are damaged, and of 1 where tissues death is certain; A is the Arrhenius pre-exponential factor for the tissues, $E_a$ is the Arrhenius activation energy for the tissue, R is the gas constant, T are the temperatures computed from equation (0.1), and $t_S$ and $t_F$ are respectively the times at which the ablation is started and finished. The scalar field $\Omega$ that results from equation (0.4) takes therefore values in the range [0,1]. It is common to consider the tissues with an $\Omega$ value >0.9 to be necrotized. The iso surface $\Omega$=0.9 describes therefore the computed ablation volume resulting from the activation of the L probes in the system.

In an embodiment and still referring to FIG. 3, system 100 may simulate the physics of MWA. The MWA thermal field may be described, without limitation, by the Pennes bioheat equation similarly to RFA:

$$\rho C \frac{\partial T}{\partial t} = \nabla \cdot k \nabla T + Q_{MW} + Q_B \tag{0.5}$$

where $Q_{MW}$ indicates now the electrical power density deposited by the application of microwave energy. Equation (0.5) allows to compute the evolution of temperatures at the ablation site when the input parameters are specified. The parameters $\rho$, C are functions of the tissues, as is $Q_B$, $Q_{MW}$ depends instead on the applied microwave energy, and can be calculated using the Maxwell equations:

$$\nabla \cdot D = \gamma \tag{0.6}$$

$$\nabla \cdot B = 0 \tag{0.7}$$

$$\nabla \times E = -\frac{\partial B}{\partial t} \tag{0.8}$$

$$\nabla \times H = \frac{\partial D}{\partial t} + J \tag{0.9}$$

where D is the electric induction vector, $\gamma$ is the electric charge distribution, B is magnetic induction, E is electric field, His magnetic field, and J is current density.

Solving equations (0.6), (0.7), (0.8), (0.9) with ad hoc boundary conditions that describe the imposed fields at the inputs of the probes and with absorbing boundary conditions and the boundaries of the computational domain allows to calculate E at the ablation site. Power density dissipated in the tissues may be $$Q_{MW} = \frac{1}{2} \sigma E \cdot E^*$$

where the symbol * indicates the complex conjugate. The computed $Q_{MW}$ can now be plugged into the bioheat equation (0.5) to calculate the temperatures in the tissues T. As temperatures in the tissues change, the properties of the tissues also change, and $Q_{MW}$ may be updated at opportune interval of times to reflect this non-linearity. Given the computed temperatures T the Arrhenius tissue damage model equation (0.4) is applied to determine which tissues are necrotized and to produce and estimated ablation volume.

In an embodiment and still referring to FIG. 4, system 100 may simulate the physics of CRYO The CRYO thermal field is described by the Pennes bioheat equation similarly to RFA:

$$\rho C \frac{\partial T}{\partial t} = \nabla \cdot k \nabla T + Q_{CRYO} + Q_B \tag{0.10}$$

where $Q_{CRYO}$ indicates now a heat density removed by ablation probes; $Q_B$ continues to model biological heat sources or sinks; in the specific case of CRYO vessels and perfusion became sources of heat, as tissues being ablated are at a temperature inferior to the temperature of blood. CRYO simulation involves only solving (0.10) given $Q_{CRYO}$ which is known from the type of probe being used and the settings of the ablation system.

In the context of CRYO a temperature field T computed from (0.10) may be directly used to indicate which tissues are ablated by taking iso-surfaces at a certain temperature (e.g. T=−30° C.).

In an embodiment, and still referring to FIG. 4, system 100 may simulate the physics of IRE. In IRE tissue damage is not caused by thermal effects like in RFA, MWA, CRYO, but by bursting of cell membranes caused by high intensity, short duration, electric pulses. Probes inserted in tissues apply voltage pulses that diffuse in the tissues according to the Laplace equation:

$$\nabla \cdot \sigma \nabla u = 0 \tag{0.11}$$

where $\sigma$ is the electrical conductivity of tissues and u is the electrical potential that develops in the tissues under the effect of the ablation probes. The multiple ablation probes are described with boundary condition:

$$V_l = u + zc_l \sigma \frac{\partial u}{\partial \hat{n}} \tag{0.12}$$

where $V_l$ is the voltage applied to the l-th probe, with l=1 . . . L where L is the number of probes, $zc_l$ is the contact impedance of the l-th probe, and $\hat{n}$ is the normal to the surface of the probe. Equation (0.11) allows computing the electric potential in the tissues u and from the electric field E=∇u. Intensity of an electric field determines whether a tissue would be subject to irreversible electroporation; a volume of ablation may be therefore determined by the iso-surface |E|=k where k is the threshold above which electroporation occurs in the specific tissue In an embodiment and still referring to FIG. 3, RFA and MWA thermal ablation types, both described by the Pennes bioheat equation (0.1) and (0.5), allows to calculate temperatures in the tissues during a period of time corresponding to the ablation. Temperatures are then fed to a tissue damage model, such as without limitation an Arrhenius tissue damage model equation (0.4), to determine which tissues are necrotized. Both types of ablation are non-linear, meaning that the temperatures in tissues cause alterations to the properties of tissues, which alter the way the RF or MW energy distributes in the tissues, which in turn alters the heating pattern. For example, at the start of the ablation tissues have a high content of water, and the power densities of deposited energy $Q_{RF}$ or $Q_{MW}$ respectively for RFA or MWA, would have an initial distribution, as temperature increases tissues would lose water content, their electrical properties would change, and as a consequence also $Q_{RF}$ or $Q_{MW}$ would change. In principle therefore, $Q_{RF}$ or $Q_{MW}$ cannot be computed just once, but at every time step used to solve the Pennes equation (0.1) and (0.5), $Q_{RF}$ or $Q_{MW}$ should ideally be re-calculated using the current properties of the tissues, which depend on the temperature and water content of the tissues. Calculating $Q_{RF}$ or $Q_{MW}$ can be computationally expensive, particularly for MWA, where the Maxwell equations (0.6), (0.7), (0.8), (0.9) need to be solved, and so this slows down considerably the simulation, wherein $Q_{RF}$ or $Q_{MW}$ are terms for RFA and MWA, respectively. These terms are pre-computed for a range of temperatures and tissue water contents values representative of the normal range of temperatures and tissues water content present in the tissues during an ablation. When applying the Pennes equation (0.1) or (0.5), the power densities of deposited energy $Q_{RF}$ or $Q_{MW}$ respectively for RFA or MWA may be looked up from a table comprising pre-computed distributions using an array, as described in detail below. Without loss of generality, in order to compute $Q_{RF}$ or $Q_{MW}$ for a range of temperatures and tissue water content values which is representative of an ablation, an ablation may be simulated with the traditional full non-linear approaches described in the preceding sections, and $Q_{RF}$ or $Q_{MW}$ may be saved, in a look-up table, at different time-points of such simulation, as tissues go through a normal—simulated—ablation cycle. Those time points may be selected, for example, to be equally spaced in time (e.g. 5 seconds apart), or $Q_{RF}$ or $Q_{MW}$ may be saved when certain temperatures are reached at certain selected points in the tissues, or when certain average temperatures in a Region of Interest (ROI) are reached, or more in general when certain conditions on the parameters that influence the distribution of power density $Q_{RF}$ or $Q_{MW}$ are met, so that sufficient samples of $Q_{RF}$ or $Q_{MW}$ are saved, providing a good sampling of the likely ranges of tissue parameters. By feeding pre-computed values of $Q_{RF}$ or $Q_{MW}$ in the Pennes equation, the simulation equation (0.1) or (0.5), the simulation of the ablation can be greatly sped-up. While a complete non-linear solution will provide in general more accuracy, feeding pre-computed terms $Q_{RF}$ or $Q_{MW}$ extracted by the look-up table will in general provide more accuracy than a linear approximation, where $Q_{RF}$ or $Q_{MW}$ are computed only for one particular set of values of the relevant parameters. Additionally, or alternatively, an advantageous method for speeding up an ablation simulation may be developed, where the terms $Q_{RF}$ or $Q_{MW}$ are fully updated periodically in the simulation, such as, but not limited to, the Pennes equation (0.1) or (0.5), is updated at every time step being simulated, but $Q_{RF}$ or $Q_{MW}$ are updated with less frequency, for example only when the temperature change in a single point in the tissues, or when the average temperature change at a set of points in the tissues exceeds a certain threshold. At the time instants in-between, the Pennes equation can be fed with the last values of $Q_{RF}$ or $Q_{MW}$, or the look-up table described above can be used again, to provide a finer simulation of the ablation.

At step 315, and continuing to refer to FIG. 3, in the context of RFA and MWA, method 300 includes determining, by the computational component, a deposited power density relating to at least an ablation parameter using at least an ablation model. As used in this disclosure "deposited power density" is a density of power deposited by an RFA or MWA as described above. Deposited power density may be determined using at least an electromagnetic algorithm. As used in this disclosure "electromagnetic algorithms" are computations that approximate an energy variation relating to a tissue volume as a function of the ablation probe 148. Electromagnetic algorithms may approximate the energy variation relating to the tissue volume using at least Maxwell's equations to calculate antenna performance, and/or electromagnetic wave propagation. Electromagnetic algorithms may include one or more integral equation solvers, wherein integral equation solvers may include, without limitation, discrete dipole approximation, method of moments element methods, finite integration techniques, fast multipole methods, plane wave time-domain methods, partial element equivalent circuit methods and the like thereof. Electromagnetic algorithms may include one or more differential equation solvers, wherein a differential equation solver may include, without limitation, a finite-difference time-domain, discontinuous time-domain method, multiresolution time-domain, finite element method, finite integration method, pseudo-spectral time domain, pseudo-spectral spatial domain, transmission line matrix, locally one-dimensional method, and the like thereof. Electromagnetic algorithms may include, without limitation, eigenmode expansion methods, physical optic methods, and/or uniform theory of diffraction methods.

In an embodiment and still referring to FIG. 3, determining the deposited power density may include detecting at least a tissue property. As used in this disclosure "tissue property" is at least a physical property of a reference point in the tissue. As used in this disclosure "physical property" is a measurable element of matter relating to a particular tissue. Physical property may include without limitation, color, hardness, thermal or electrical physical property of region of interest, and the like thereof. Tissue types may include, without limitation, healthy tissues, diseased tissues, parenchyma, malignant tissues, connective tissue, epithelial tissue, muscle tissue, and nervous tissue. As a non-limiting example tissue property may identify the current tissue water content during an ablation of the tissue volume. Tissue property may be identified by one or more arrays using an array indexing operation. As used in this disclosure "array" is a data structure consisting of a collection of values and/or variables associated with the physical property of the tissue volume. As a non-limiting example, an array may include a lookup table that retrieves a physical property or other value from a memory. Physical property may include precalculated tissue properties. Alternatively or additionally, physical property may include a deposited power density such as $Q_{RF}$ and/or $Q_{MW}$ as described above. As used in this disclosure "array indexing operation" is a key that at least extracts individual values, variables, and or representations from an array. As a non-limiting example a multidimensional array may relate to a plurality of physical properties or a plurality of human tissues, wherein an array indexing operation extracts the deposited power density of a particular tissue relating to the kidneys given a particular value of water content in the tissue. Tissue property may be detected by at least a sensor feedback element. As used in this disclosure "sensor feedback element" is an element relating to one or more sensor inputs as a function of the ablation. As a non-limiting example sensor feedback element may relate to the temperature at a particular point in the ablation volume. Where a lookup table or other data storage facility is used, including without limitation as described in this disclosure, physical properties may be used to retrieve other physical properties and/or deposited energy density, temperature, and/or ablation volume parameters. For instance thermal properties of tissue may be looked up and/or retrieved from such data storage facilities based on tissue water content. Persons skilled in the art, upon reviewing the entirety of this disclosure, will be aware of various parameters relating to tissue properties and/or ablation that may be used to predict and/or derive other such parameters; any such interrelations may be stored and/or retrieved in data storage facilities such as lookup tables as described in this disclosure.

Further referring to FIG. 3, one or more physical property values stored in a look-up table may be linked to, and thus retrievable according to, one or more other parameters of an ablation environment. Such parameters may include tissue type, one or more measured or simulated tissue qualities, one or more measured or simulated current temperature values of the tissue, or the like. Computational component may query look-up table using such parameters. For instance, computational component may query look-up table using measurements of temperature and/or other parameters captured using sensors at or near ablation site, using measurements of temperature and/or other parameters generated by a simulation, or any combination thereof. In an embodiment, a single look-up table may be utilized for a plurality of ablation sites; for instance and without limitation, where multiple probes are inserted into a patient's tissue to ablate a larger area than reachable for a single probe, look-up table may be used to determine a physical parameter for tissue in a vicinity of each probe of the multiple probes. In this way, physical parameters affecting subsequent calculations such as temperature calculations may be retrieved in a computationally efficient, resource-efficient manner. As a non-limiting example, determining a deposited power density may include retrieving at least a value from a look-up table as a function of at least an ablation parameter, and determining the deposited power density as a function of the at least a value; the at least a value may include a deposited power density. The at least an ablation parameter may be generated using the at least an ablation model and/or may be detected using at least a sensor. Determining deposited power density may include detecting at least a tissue property, such as at least a physical property of a reference point in the tissue. Detecting at least a tissue property may include identifying, in an array, a tissue property using an array indexing operation. Detecting at least a tissue property may include gaining at least a sensor feedback element. Detecting at least a tissue property may include identifying at least a thermal element and/or attribute of a region of interest.

In an embodiment and still referring to FIG. 3, determining the deposited power density may include identifying at least a status parameter as a function of a status array. As used in this disclosure "status parameter" is at least a parameter relating to a forward movement of an ablation. As a non-limiting example status parameter may indicate that an ablation is 80% completed. As a further non-limiting example status parameter may indicate that an ablation is currently 5 minutes into the procedure, or that the water content of a particular tissue has dropped by a certain amount as a consequence of the heating and evaporation.

With further reference to FIG. 3, at step 320, computational component may identify, by the computational component, an ablation volume, defined as a volume of tissue necrotized during an ablation procedure performed at the ablation site based on the heat distribution. An ablation volume may be computed using models that reflect the physics of the ablation. Ablation volume may be determined as a function of at least an ablation parameter and at least an ablation model. As used in this disclosure "ablation parameter" is one or more parameters that at least alter the ablation volume. As a non-limiting example ablation parameter may include a thermal element, wherein a thermal element is a parameter relating to thermal properties of a tissue volume, such as without limitation a specific heat of a tissue volume. As a further non-limiting example a thermal element may relate to the melting point and/or vaporization point of a tissue volume. As a further non-limiting example, thermal element may relate to an atomic resonance of the tissue volume, wherein an atomic resonance relates to the level of energy required to at least raise an electron from a first lower energy orbital to a second higher energy of orbital. A thermal property may affect a degree to which a given amount of energy or other treatment modifies temperature of an ablation volume, which may in turn be used to predict necrotized areas more effectively. As used in this disclosure "ablation model" is an algorithm that at least identifies one or more magnitudes of varying energies that relate to the ablation volumes. Ablation model may identify one or more tissue volumes that have an elevated temperature, wherein the elevated temperature may be determined as a function of a convection/conduction process. As a non-limiting example, ablation model may include one or more thermal algorithms. As used in this disclosure "thermal algorithms" are computations that identify a tissue volume temperature as a function of the ablation probe 148 and/or ablation controller settings and/or other parameters and/or settings relating to ablation.

In an embodiment, this may be performed by using a bioheat equation, as described above, to determine isolines and/or surfaces representing boundaries of regions heated to a minimum temperature for necrotization of tissues; for instance, an isoline or surface within which all tissues are at or above 60 degrees Celsius may be identified. This may, in a non-limiting example, result in a reduced primary ablation volume, because a lesser quantity of heat energy may be deposited in such tissues. Alternatively or additionally, necrotization may be modeled using an Arrhenius model that looks at temperature and time of exposure to a given temperature. In an embodiment, a bioheat equation may be used to calculate a temperature at each point in an ablation site, and the temperature may be computed at discrete time intervals, such as without limitation every 1 second during a 6-minute ablation. For each point a temporal evolution of the temperature may be fed to the Arrhenius model which may indicate a 0 to 100% probability of cell death for that point of tissues; the ablation/necrotized tissue volume may be taken to be a volume of tissue estimated to have 90% death probability. Alternatively or additionally, a plurality of data entries describing past procedures may be used as training data, which may include any training data as described in further detail above, for instance any procedural and/or modeled parameters, outputs, or the like as described in this disclosure, including without limitation power level and/or temperature delivered to a given site, two or three-dimensional depictions of ablation sites, or the like with identifications entered by users or other systems and/or processes of necrotized tissues, one or more pixels, voxels, and/or coordinates contained in and/or located at necrotized tissues, or the like; prediction of necrotized volumes may be performed using any form of machine learning and/or deep learning as described in further detail below, including without limitation lazy learning, neural net processes, and/or generation of one or more machine-learning models.

Referring now to FIG. 4, an exemplary embodiment of a method 400 of simulating an ablation volume is illustrated.

At step 405, a computational component receives an ablation probe ablative energy data; this may be implemented, without limitation, as described above in reference to FIGS. 1-3.

Still referring to FIG. 4, at step 410, computational component calculates an electromagnetic field deposited power density from the ablation probe in a first model ablation volume; this may be implemented, without limitation, as described above in reference to FIGS. 1-3.

With continued reference to FIG. 4, at step 415, computational component calculates a thermal distribution from the ablation probe in a second model ablation volume, where the first model ablation volume is smaller than the second model ablation volume; this may be implemented, without limitation, as described above in reference to FIGS. 1-3.

At step 420, and still referring to FIG. 4, computational component determines boundaries of the ablation volume according to the calculations of the electromagnetic field deposited power density and the thermal distribution from the ablation probe in the ablation probe; this may be implemented, without limitation, as described above in reference to FIGS. 1-3

Figure 5:
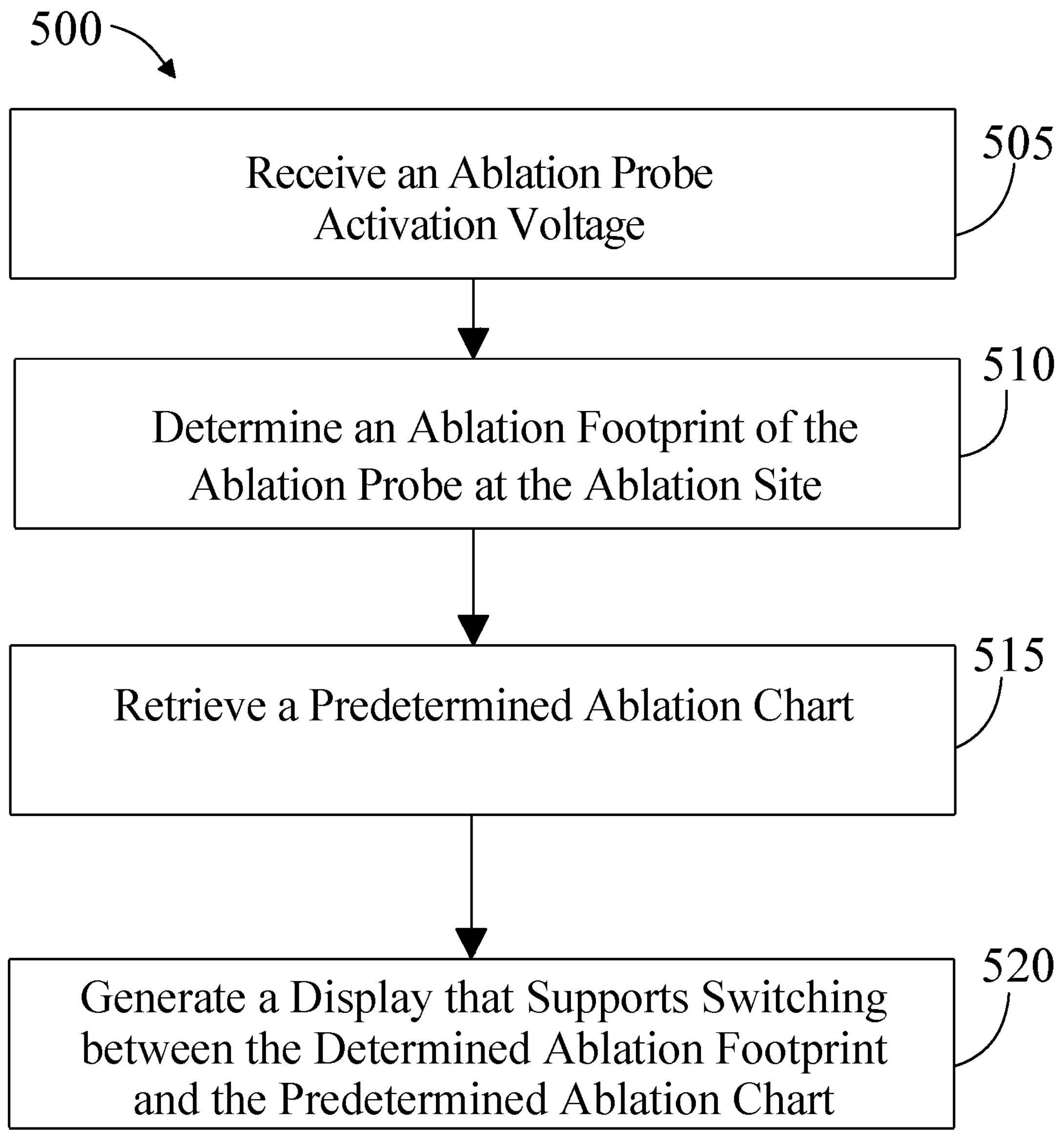
FIG. 5 is a flow diagram illustrating an exemplary embodiment of a method of modeling a necrotized tissue volume in an ablation procedure

Referring now to FIG. 5, an exemplary embodiment of a method 500 of determining an ablation footprint of an ablation site is illustrated. At step 505, a computational component receives an ablation probe ablative energy data associated with using an ablation probe at an ablation site; this may be implemented, without limitation, as described above in reference to FIGS. 1-4.

At step 510, and still referring to FIG. 5, computational component determines an ablation footprint of the ablation probe at the ablation site; this may be implemented, without limitation, as described above in reference to FIGS. 1-4. For instance, and without limitation, determining may include determining a representation of a necrotic area of the ablation site as a function of the ablation probe ablative energy data. In an embodiment, determining the ablation footprint may include determining a plurality of ablation volumes, each of which may be determined in any manner described in this disclosure. Computational component may aggregate a plurality of ablation volumes; this may be performed in any manner described in this disclosure. In an embodiment, plurality of ablation volumes may correspond to a plurality of probe positions, which plurality may include an instant probe position at ablation site. Computational component may determine ablation footprint as a function of aggregated plurality of ablation volumes. For instance, ablation volume may be and/or include aggregated plurality of ablation volumes.

At step 515, and continuing to refer to FIG. 5, computational component retrieves a predetermined ablation chart, wherein the predetermined ablation chart includes a predetermined necrotic area as a function of the ablation probe and the voltage applied.

Still referring to FIG. 5, computational component may be further configured to identify a plurality of predetermined necrotic volumes as a function of the predetermined ablation chart; each may be determined as described in this disclosure. In an embodiment, plurality of ablation predetermined necrotic volumes may correspond to a plurality of probe positions, which plurality may include an instant probe position at ablation site. This may be accomplished using a plurality of charts corresponding to a plurality of probe positions and/or at least a chart that corresponds to two or more probe positions. Computational component may aggregate the plurality of ablation plurality of predetermined necrotic volumes. Computational component may determine the predetermined necrotic area as a function of the aggregated plurality of predetermined necrotic volumes. For instance, predetermined necrotic area may be and/or include aggregated plurality of predetermined necrotic volumes.

At step 520, and still referring to FIG. 5, computational component generates a display of the ablation footprint and the predetermined ablation chart, where the display supports switching between the determined ablation footprint and the predetermined ablation chart; this may be implemented, without limitation, as described above in reference to FIGS. 1-4. Display of predetermined ablation chart and/or determined ablation footprint may display results of single ablations and/or cumulative effects of multiple ablations; for instance, previously predicted and/or detected ablation volumes may be added to and/or combined with predetermined ablation chart data and/or determined ablation footprint data to determine a currently predicted and/or estimated ablation volume, which may be displayed in display. As before, predictions and/or estimations based on predetermined ablation chart may be displayed in a view illustrating such predetermined volume-based predictions and/or estimations, whereas predictions and/or estimations based on determined ablation footprint may be displayed in a view illustrating such determined ablation footprint-based predictions and/or estimations.

Further referring to FIG. 5, displayed information in either category and/or view may indicate which tissues have been ablated, which tissues are going to be ablated, and/or target tissues to be ablated.

Figure 6:
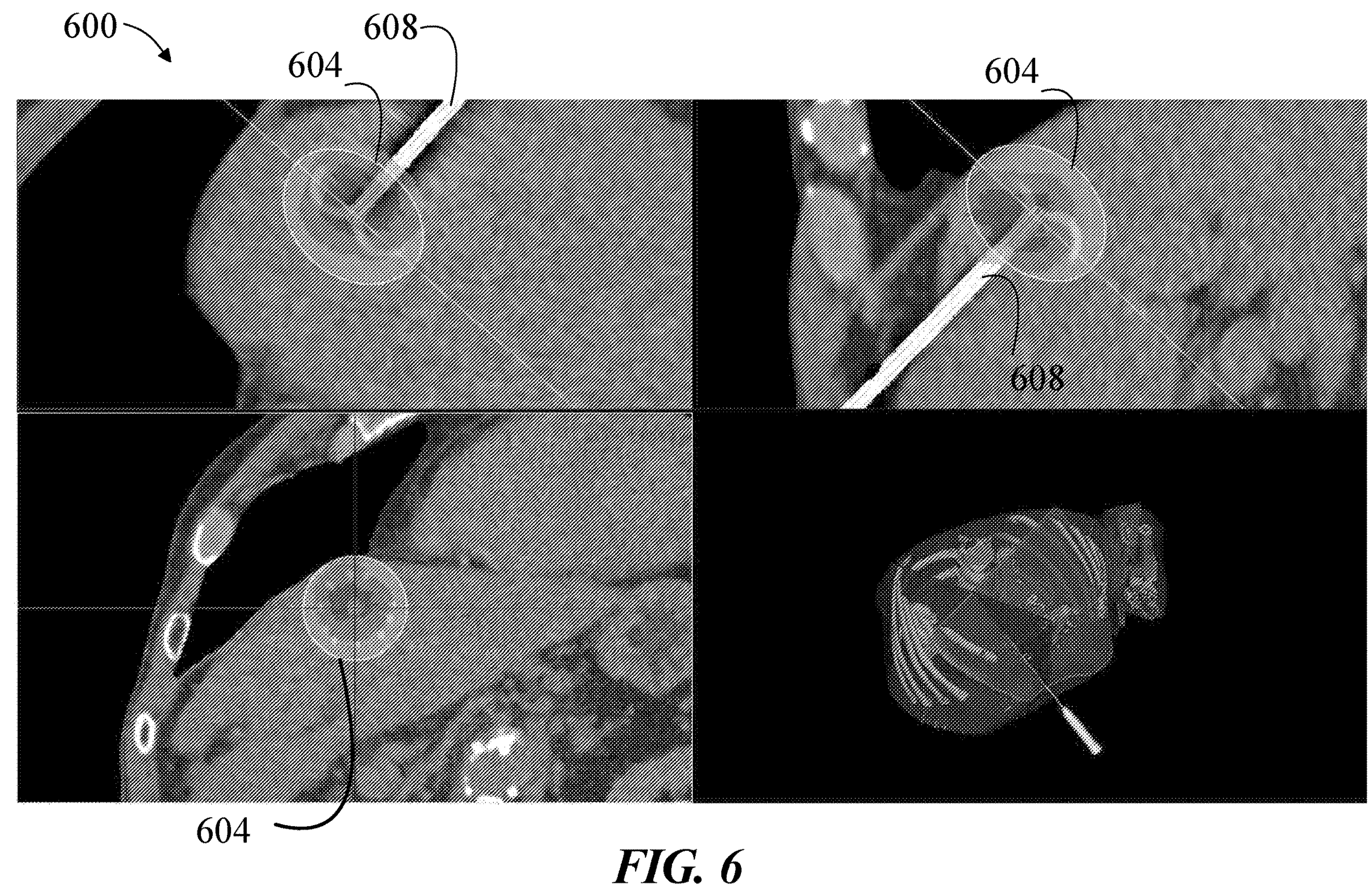
FIG. 6 is a screenshot illustrating an exemplary embodiment of a display.

Referring now to FIG. 6, an exemplary screenshot 600 of a surgical guidance application illustrating a predetermined ablation chart is illustrated. Predetermined ablation chart may include one or more predicted ablation or "kill" volumes, 604, which may describe an idealized and/or regular shape around an image of a probe 608; for instance, and as illustrated in FIG. 6, idealized shape may have a substantially elliptical cross-section. In an embodiment, predicted ablation volumes in predetermined ablation chart may not correspond well to likely actual ablation volumes; in particular, kill chart volumes may overestimate and/or underestimate chances that a given volume of tissue will be entirely or partially within an ablation volume.

Figure 7:
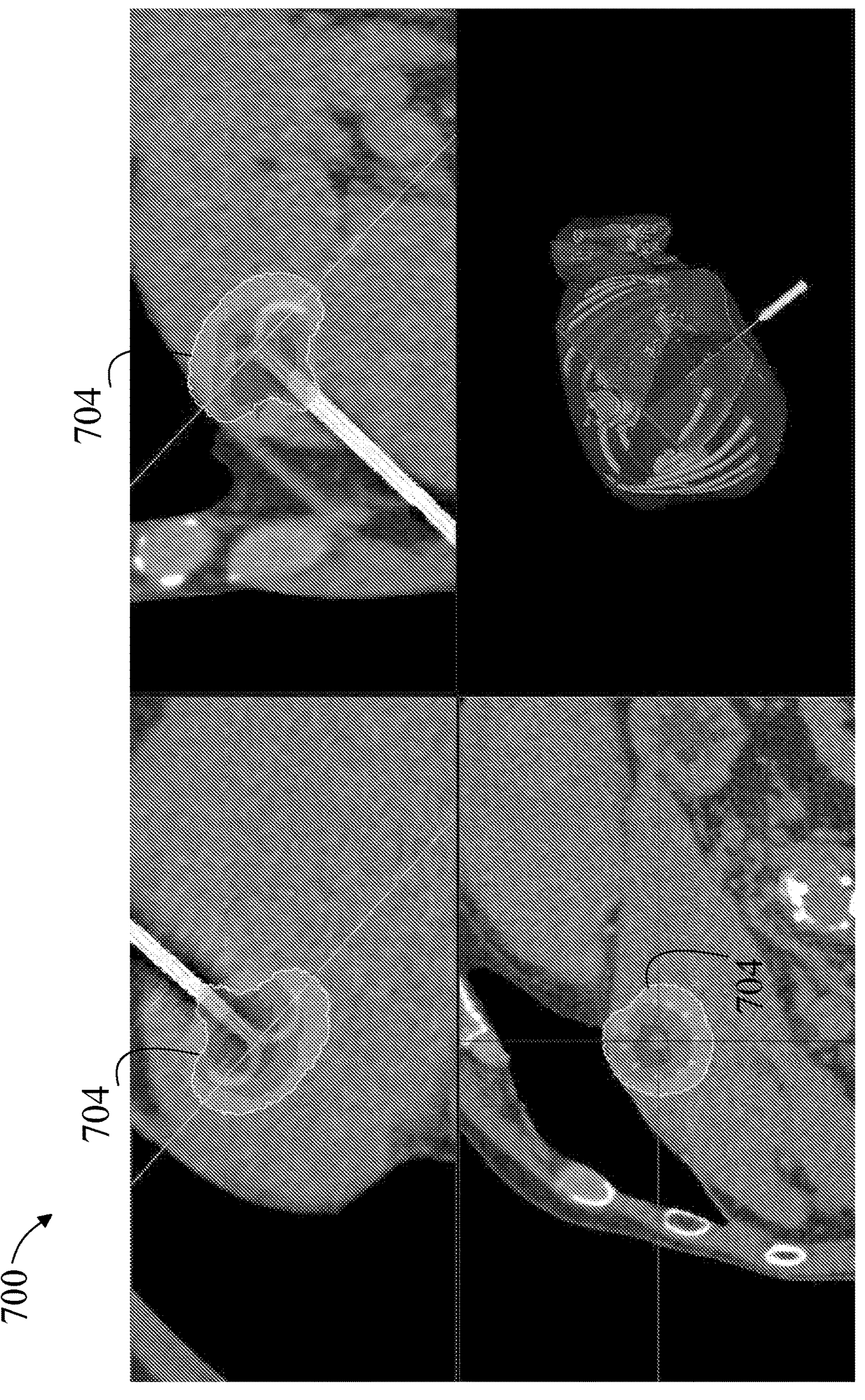
FIG. 7 is a screenshot illustrating an exemplary embodiment of a display.

Referring now to FIG. 7, an exemplary embodiment of a screenshot 700 of a surgical guidance application display displaying ablation footprint 704 is provided. Ablation footprint may predict necrotized tissues based on simulating physics of the ablation—this may represent a more realistic representation of the ablation footprint, enabling a user to more accurately predict which tissue will be necrotized, which in turn may enable the user to kill or remove target tissue accurately while minimizing damage to non-target tissue. A user may find it expedient to alternate the view with a representation based on pre-computed charts as described above in order to evaluate indications of algorithms predicting an ablation footprint against indications of a manufacturer.

Figure 8:
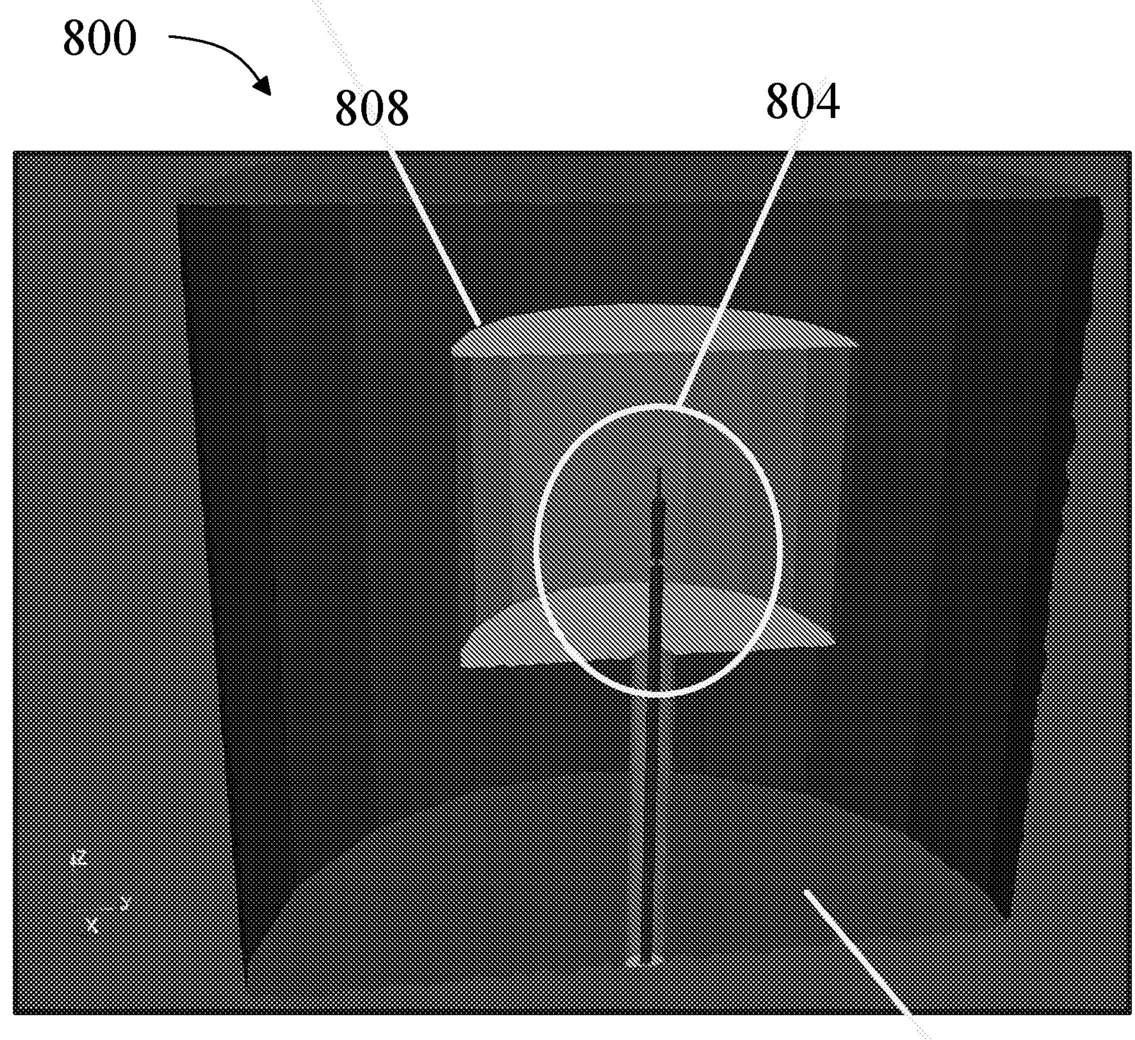
FIG. 8 is an exemplary embodiment of a simulation and/or model of an ablation volume.

Now referring to FIG. 8, an exemplary embodiment of a simulation 800 and/or model of an ablation volume is depicted. Simulation and/or model may include a microwave antenna 804 and/or probe. Simulation and/or model may include a computational domain for an electromagnetic field, which may include any electromagnetic field as described above that may be emitted by an ablation probe 148. Computational domain may have a boundary 808, which may include any surface of any three-dimensional geometric figure, including without limitation a substantially cylindrical surface. A computational component operating on simulation and/or model may perform computation of electromagnetic field only within boundary 808; in other words, computation may be performed only for a volume containing and/or surrounding antenna/probe 804 and bounded by boundary 808. Simulation and/or model may include a computational domain for a thermal field, which may be bounded by a second boundary 812. Computational domain for thermal field may define a volume within which thermal field is computed, estimated, or otherwise modeled. Computational domain for thermal field may include computational domain for electromagnetic field; that is, in the latter domain, computations may be performed for both thermal and electromagnetic fields, while in the portion of computational domain for thermal field not containing computational domain for electromagnetic field, only thermal field-related computation may be performed.

Figure 9:
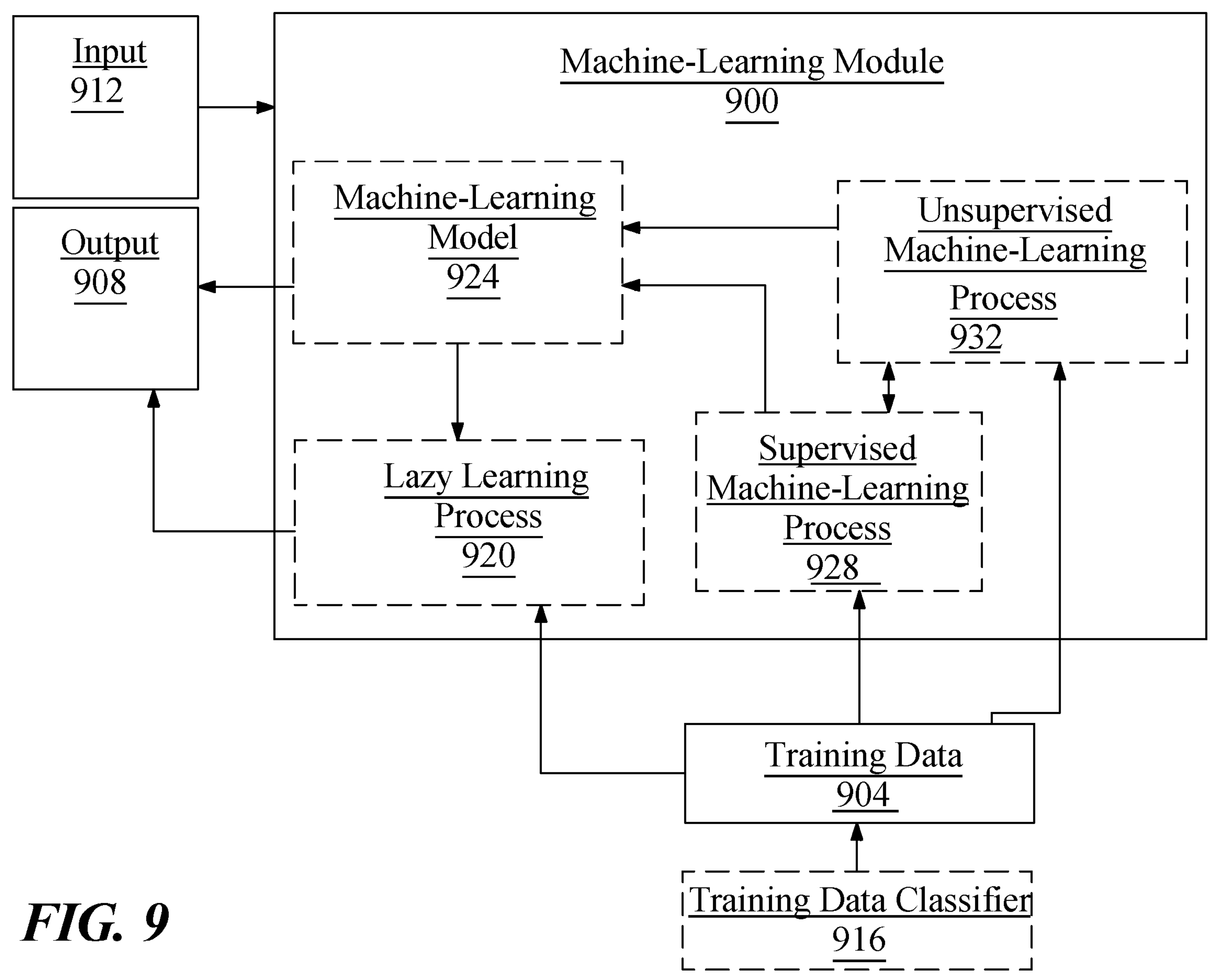
FIG. 9 is block diagram of an exemplary embodiment of a machine-learning module.

Referring now to FIG. 9, an exemplary embodiment of a machine-learning module 900 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 904 to generate an algorithm that will be performed by a computational component/module to produce outputs 908 given data provided as inputs 912; this is in contrast to a non-machine learning software program where the commands to be executed are determined in advance by a user and written in a programming language.

Still referring to FIG. 9, "training data," as used herein, is data containing correlations that a machine-learning process may use to model relationships between two or more categories of data elements. For instance, and without limitation, training data 904 may include a plurality of data entries, each entry representing a set of data elements that were recorded, received, and/or generated together; data elements may be correlated by shared existence in a given data entry, by proximity in a given data entry, or the like. Multiple data entries in training data 904 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 904 according to various correlations; correlations may indicate causative and/or predictive links between categories of data elements, which may be modeled as relationships such as mathematical relationships by machine-learning processes as described in further detail below. Training data 904 may be formatted and/or organized by categories of data elements, for instance by associating data elements with one or more descriptors corresponding to categories of data elements. As a non-limiting example, training data 904 may include data entered in standardized forms by persons or processes, such that entry of a given data element in a given field in a form may be mapped to one or more descriptors of categories. Elements in training data 904 may be linked to descriptors of categories by tags, tokens, or other data elements; for instance, and without limitation, training data 904 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 9, training data 904 may include one or more elements that are not categorized; that is, training data 904 may not be formatted or contain descriptors for some elements of data. Machine-learning algorithms and/or other processes may sort training data 904 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 904 to be made applicable for two or more distinct machine-learning algorithms as described in further detail below. Training data 904 used by machine-learning module 900 may correlate any input data as described in this disclosure to any output data as described in this disclosure. As a non-limiting illustrative thermal physical properties of tissues may be inputted to output ablation volumes Further referring to FIG. 9, training data may be filtered, sorted, and/or selected using one or more supervised and/or unsupervised machine-learning processes and/or models as described in further detail below; such models may include without limitation a training data classifier 916. Training data classifier 916 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 900 may generate a classifier using a classification algorithm, defined as a processes whereby a computational component and/or any module and/or component operating thereon derives a classifier from training data 904. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 916 may classify elements of training data to sub-categories of physical properties such as thermal constants, dielectric constants, density constants, and the like thereof.

Still referring to FIG. 9, machine-learning module 900 may be configured to perform a lazy-learning process 920 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 904. Heuristic may include selecting some number of highest-ranking associations and/or training data 904 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 9, machine-learning processes as described in this disclosure may be used to generate machine-learning models 924. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 924 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 924 may be generated by creating an artificial neural network, such as a convolutional neural network comprising an input layer of nodes, one or more intermediate layers, and an output layer of nodes. Connections between nodes may be created via the process of "training" the network, in which elements from a training data 904 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 9, machine-learning algorithms may include at least a supervised machine-learning process 928. At least a supervised machine-learning process 928, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include thermal properties as described above as inputs, tissue ablation as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 904. Persons skilled in the art, upon reviewing the entirety of this disclosure, will be aware of various possible variations of at least a supervised machine-learning process 928 that may be used to determine relation between inputs and outputs. Supervised machine-learning processes may include classification algorithms as defined above.

Further referring to FIG. 9, machine learning processes may include at least an unsupervised machine-learning processes 932. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 9, machine-learning module 900 may be designed and configured to create a machine-learning model 924 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 9, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
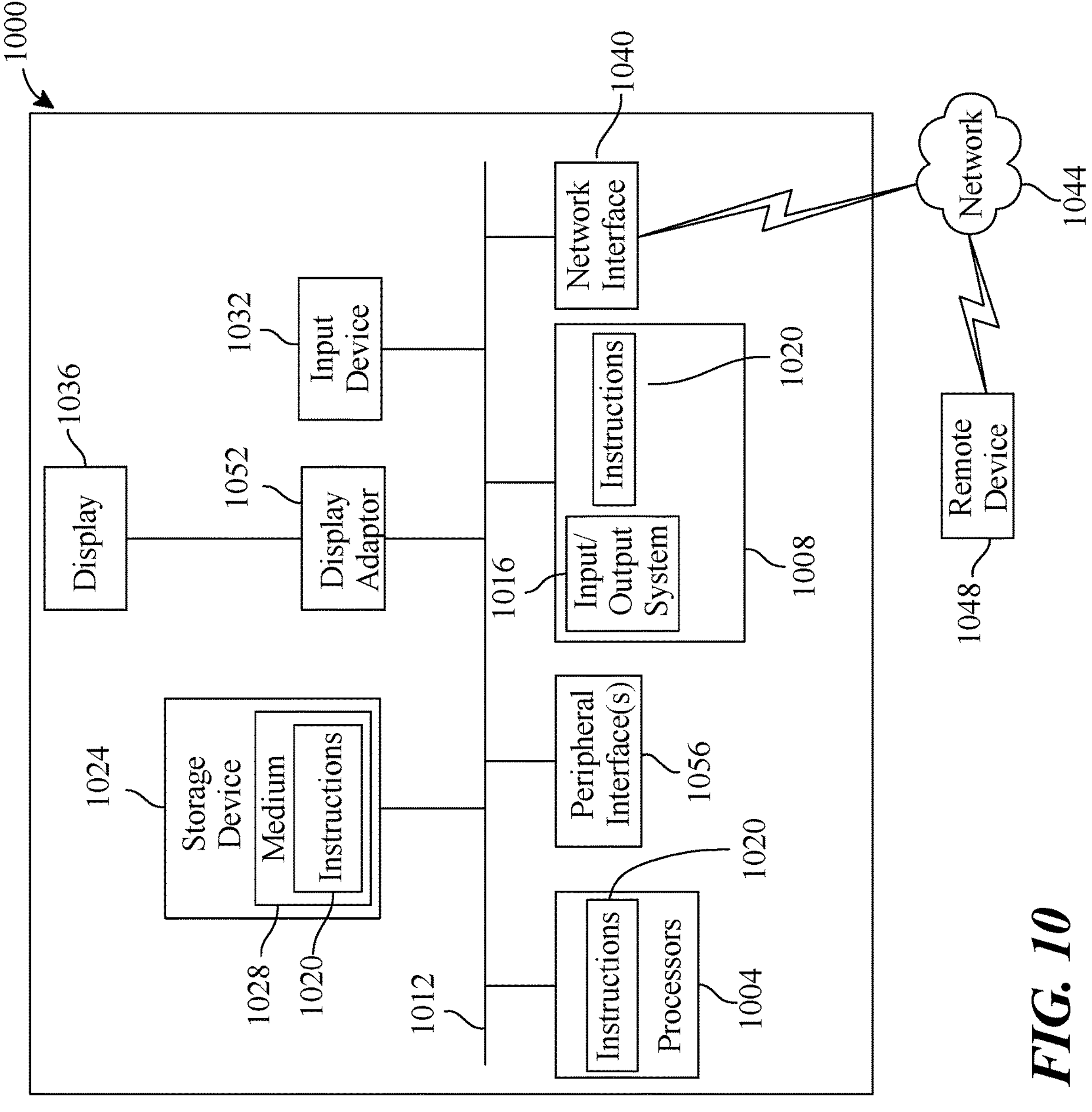
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC)

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for simulating an ablation volume, the system comprising a computational component, the computational component being configured to:

receive an ablation probe ablative energy data;

calculate an electromagnetic field deposited power density from the ablation probe in a first model ablation volume;

calculate a thermal distribution resulting from the deposited power density from the ablation probe in a second model ablation volume, wherein the first model ablation volume is smaller than the second model ablation volume; and determine boundaries of the ablation volume according to the calculations of the electromagnetic field deposited power density and the thermal distribution from the ablation probe.

2. The system of claim 1, wherein the computational component calculates the deposited power density by:

retrieving a value from a look-up table as a function of an ablation parameter; and determining the deposited power density as a function of the value.

3. The system of claim 2, wherein the ablation parameter is detected using a sensor.

4. The system of claim 1, wherein calculating the deposited power density comprises detecting a tissue property of tissue located at an ablation site, wherein the tissue property corresponds to a physical property of a reference point in the tissue.

5. The system of claim 4, wherein detecting the tissue property further comprises identifying, in an array, the tissue property using an array indexing operation.

6. The system of claim 4, wherein detecting the tissue property further comprises identifying a thermal element of a region of interest in the tissue.

7. The system of claim 1, wherein calculating the deposited power density further comprises identifying at least a status parameter as a function of a status array.

8. The system of claim 1, wherein calculating the deposited power density further comprises generating a thermal impact on a human tissue and determining the deposited power density as a function of the thermal impact on the human tissue.

9. The system of claim 1 further comprising a radiological machine in communication with the computational component.

* * * * *